United States Patent
Taniguchi

(10) Patent No.: US 11,819,010 B2
(45) Date of Patent: Nov. 21, 2023

(54) SEX IDENTIFICATION DEVICE FOR FERTILIZED EGGS, SEX IDENTIFICATION METHOD FOR FERTILIZED EGGS, AND PROGRAM

(71) Applicant: Nobuhide Yagi, Tokyo (JP)

(72) Inventor: Ryosuke Taniguchi, Nagasaki (JP)

(73) Assignee: Nobuhide Yagi, Tokyo (JP)

( * ) Notice: Subject to any disclaimer, the term of this patent is extended or adjusted under 35 U.S.C. 154(b) by 405 days.

(21) Appl. No.: 17/292,228

(22) PCT Filed: Nov. 5, 2019

(86) PCT No.: PCT/JP2019/043191
§ 371 (c)(1),
(2) Date: May 7, 2021

(87) PCT Pub. No.: WO2020/095868
PCT Pub. Date: May 14, 2020

(65) Prior Publication Data
US 2021/0400922 A1    Dec. 30, 2021

(30) Foreign Application Priority Data

Nov. 7, 2018  (WO) ................. PCT/JP2018/041388

(51) Int. Cl.
*A01K 43/04*     (2006.01)
*G06T 7/62*      (2017.01)
(Continued)

(52) U.S. Cl.
CPC ............. *A01K 43/04* (2013.01); *G01B 11/24* (2013.01); *G01N 33/08* (2013.01); *G06T 7/12* (2017.01);
(Continued)

(58) Field of Classification Search
CPC ...... A01K 43/04; A01K 45/007; A01K 45/00; A01K 43/00; A01K 43/06; G01B 11/24;
(Continued)

(56) References Cited

U.S. PATENT DOCUMENTS 6,029,080 A * 2/2000 Reynnells ............ G01R 33/483
                                          600/407
7,167,579 B2 * 1/2007 Taniguchi ............ A01K 43/06
                                          119/713
(Continued)

FOREIGN PATENT DOCUMENTS

AT          404051 T      8/2008
CN         1449655 A     10/2003
(Continued)

OTHER PUBLICATIONS

Stephane Nicolau, "Extended European Search Report for EP Application No. 19882318.9", EPO, Germany.
(Continued)

*Primary Examiner* — Michael S Osinski
(74) *Attorney, Agent, or Firm* — Bridgeway IP Law Group, PLLC; Jihun Kim

(57) ABSTRACT

Proposed is a technique for performing sexing of a fertilized egg with a high sexing rate at a high speed, based on image data obtained by photographing a contour of the egg. In particular, a fertilized egg sexing method, a fertilized egg sexing apparatus and a program for making a female/male judgment of a fertilized egg according to a contour of the fertilized egg by a computer are proposed. The fertilized egg sexing method includes: extracting the contour based on image data obtained by photographing the fertilized egg at different angles, calculating a short radial from the contour, calculating short radial phase differences corresponding to
(Continued)

photographing at the angles, and making a female/male judgment using the short radial phase differences.

7 Claims, 29 Drawing Sheets

(51) Int. Cl.
  *G06T 7/12* (2017.01)
  *G06T 7/174* (2017.01)
  *G01B 11/24* (2006.01)
  *G01N 33/08* (2006.01)
(52) U.S. Cl.
  CPC .............. *G06T 7/174* (2017.01); *G06T 7/62* (2017.01); *G06T 2207/20168* (2013.01)
(58) Field of Classification Search
  CPC ............ G01B 2210/54; G01N 33/08; G01N 21/3563; G01N 33/085; G06T 7/12; G06T 7/174; G06T 7/62; G06T 2207/20168; G06T 7/0004; G06T 2207/30128; G06T 2207/10024; G06T 7/0012; G06T 7/11; G06T 2207/10056; G06T 2207/20024; G06T 2207/30004; G06T 2207/20076; G06T 2207/30024; G06T 2207/30044
  See application file for complete search history.

(56) References Cited

U.S. PATENT DOCUMENTS

| | | | | |
|---|---|---|---|---|
| 8,364,247 B2* | 1/2013 | Opitz | ................... | A01K 45/007 600/478 |
| 8,624,190 B2* | 1/2014 | Steiner | ................. | G01N 21/552 250/339.08 |
| 9,435,732 B2* | 9/2016 | Rozenboim | ............ | G01N 33/08 |
| 10,607,338 B2* | 3/2020 | Ngadi | ..................... | G06F 18/24 |
| 11,688,064 B2* | 6/2023 | Ngadi | ....................... | G06T 7/40 382/108 |
| 11,703,457 B2* | 7/2023 | Yang | ....................... | G01S 17/42 348/125 |
| 2003/0185422 A1 | 10/2003 | Taniguchi | | |
| 2004/0040515 A1 | 3/2004 | Taniguchi | | |
| 2014/0112557 A1* | 4/2014 | Santamaria-Pang | ...... | G06T 7/12 382/128 |
| 2019/0095678 A1* | 3/2019 | Aragaki | .................... | G06T 7/50 |
| 2022/0132811 A1* | 5/2022 | Mizrach | ................. | A61B 5/004 119/713 |
| 2023/0088338 A1* | 3/2023 | Baker | ................. | G01N 15/1012 |

FOREIGN PATENT DOCUMENTS

| | | |
|---|---|---|
| EP | 1348334 A1 | 10/2003 |
| HK | 1059353 A | 7/2004 |
| JP | 2003-274791 A | 9/2003 |
| JP | 2005-87123 A | 4/2005 |
| JP | 2010-038897 A | 2/2010 |
| JP | 2011-142866 A | 7/2011 |
| KR | 10-2003-0077994 A | 10/2003 |
| KR | 10-0533291 B1 | 12/2005 |
| TW | 200307810 A | 12/2003 |

OTHER PUBLICATIONS

Nozaki, Koichi, "Study about realization and inspection of a fertilized egg by high-definition digital image processing", Grant-in-Aid for Scientific Research, Final Research Report, Jun. 2, 2015, 4 pages, http://kaken.nii.ac.jp/ja/file/KAKENHI-PROJECT-25540073/25540073seika.pdf.

International Search Report/Written Opinion of the International Searching Authority, International Application No. PCT/JP2018/041388, dated Jan. 8, 2019, 6 pages.

International Search Report/Written Opinion of the International Searching Authority, International Application No. PCT/JP2019/043191, dated Jan. 28, 2020, 6 pages.

* cited by examiner

CONTOUR AND CONTOUR DISTORTION

VELOCITY (ANGULAR VELOCITY)

| Meas-No | SEX | IncSR0 | IncSR90 | PD_YRL | PD_SERL | PD_TRFRL | PD_TRARL |
|---|---|---|---|---|---|---|---|
| E1011 | ♀ | Left | Left | Lead | Lead | Lag | Lag |
| E1012 | ♀ | Left | Left | Lead | Lead | Lag | Lag |
| E1013 | ♀ | Left | Left | Lead | Lead | Lag | Lag |
| E1014 | ♀ | Left | Left | Lead | Lead | Lag | Lag |
| E3509 | ♂ | Left | Left | Lag | Lag | Lead | Lead |
| E3510 | ♂ | Left | Left | Lag | Lag | Lead | Lead |
| E3511 | ♂ | Left | Left | Lag | Lag | Lead | Lead |
| E3512 | ♂ | Left | Left | Lag | Lag | Lead | Lag |

| Meas-No | SEX | IncSR0 | IncSR90 | PD_YRL | PD_SERL | PD_TRFRL | PD_TRARL |
|---|---|---|---|---|---|---|---|
| E1015 | ♀ | Left | Right | Lag | Lag | Lead | Lead |
| E1016 | ♀ | Left | Right | Lag | Lag | Lead | Lead |
| E1001 | ♀ | Left | Right | Lag | Lag | Lead | Lead |
| E1002 | ♀ | Left | Right | Lag | Lag | Lead | Lead |
| E3513 | ♂ | Left | Right | Lead | Lead | Lag | Lag |
| E3514 | ♂ | Left | Right | Lead | Lead | Lag | Lag |
| E3515 | ♂ | Left | Right | Lead | Lead | Lag | Lag |
| E3516 | ♂ | Left | Right | Lead | Lead | Lag | Lead |

| Meas-No | SEX | IncSR0 | IncSR90 | PD_YRL | PD_SERL | PD_TRFRL | PD_TRARL |
|---|---|---|---|---|---|---|---|
| E1007 | ♀ | Right | Left | Lag | Lag | Lead | Lead |
| E1008 | ♀ | Right | Left | Lag | Lag | Lead | Lead |
| E1009 | ♀ | Right | Left | Lag | Lag | Lead | Lead |
| E1010 | ♀ | Right | Left | Lag | Lag | Lead | Lead |
| E3505 | ♂ | Right | Left | Lead | Lead | Lag | Lag |
| E3506 | ♂ | Right | Left | Lead | Lead | Lag | Lag |
| E3507 | ♂ | Right | Left | Lead | Lead | Lag | Lag |
| E3508 | ♂ | Right | Left | Lead | Lead | Lag | Lead |

| Meas-No | SEX | IncSR0 | IncSR90 | PD_YRL | PD_SERL | PD_TRFRL | PD_TRARL |
|---|---|---|---|---|---|---|---|
| E1003 | ♀ | Right | Right | Lead | Lead | Lag | Lag |
| E1004 | ♀ | Right | Right | Lead | Lead | Lag | Lag |
| E1005 | ♀ | Right | Right | Lead | Lead | Lag | Lag |
| E1006 | ♀ | Right | Right | Lead | Lead | Lag | Lag |
| E3501 | ♂ | Right | Right | Lag | Lag | Lead | Lead |
| E3502 | ♂ | Right | Right | Lag | Lag | Lead | Lead |
| E3503 | ♂ | Right | Right | Lag | Lag | Lead | Lead |
| E3504 | ♂ | Right | Right | Lag | Lag | Lead | Lag |

FIG. 2

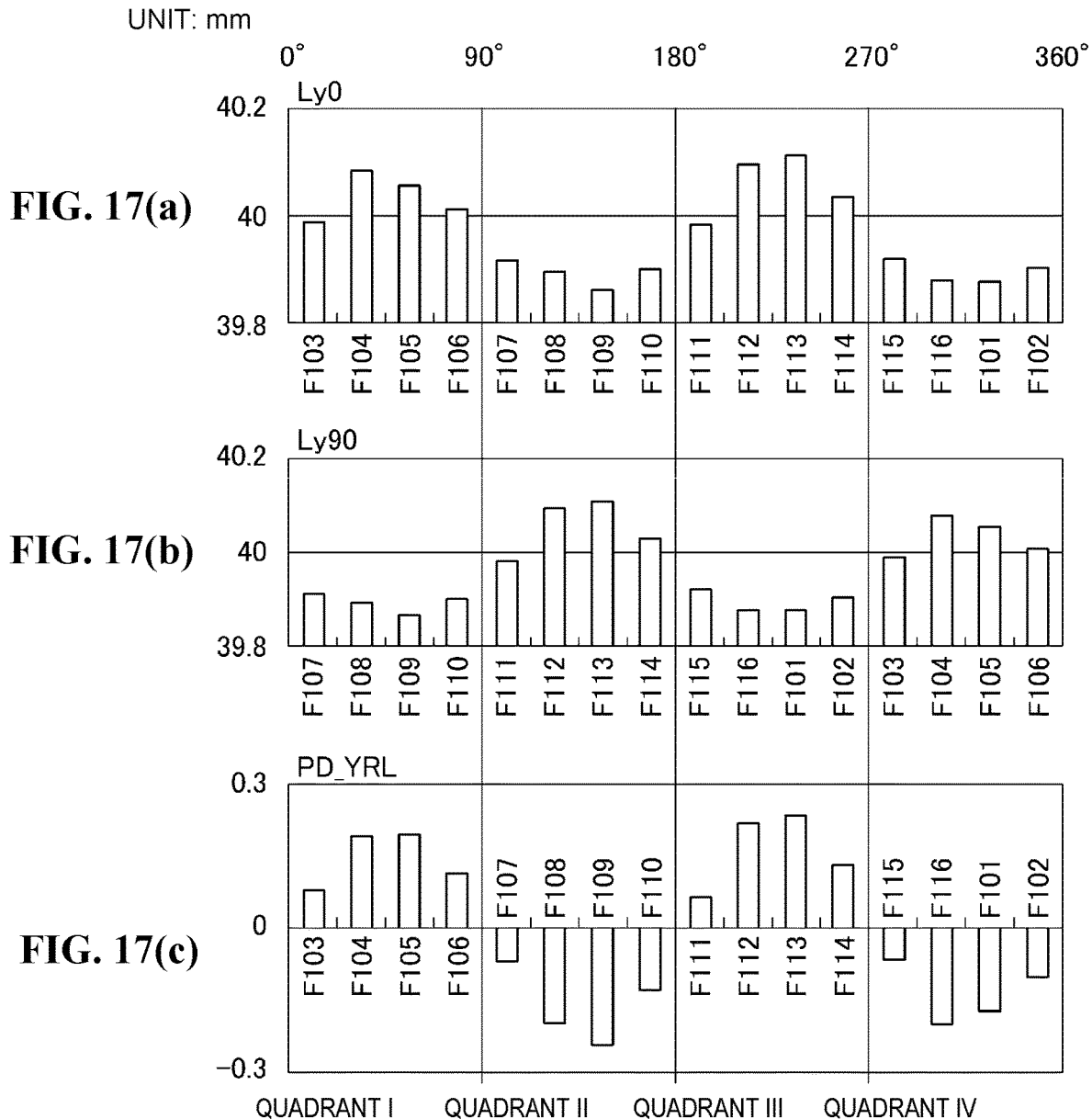

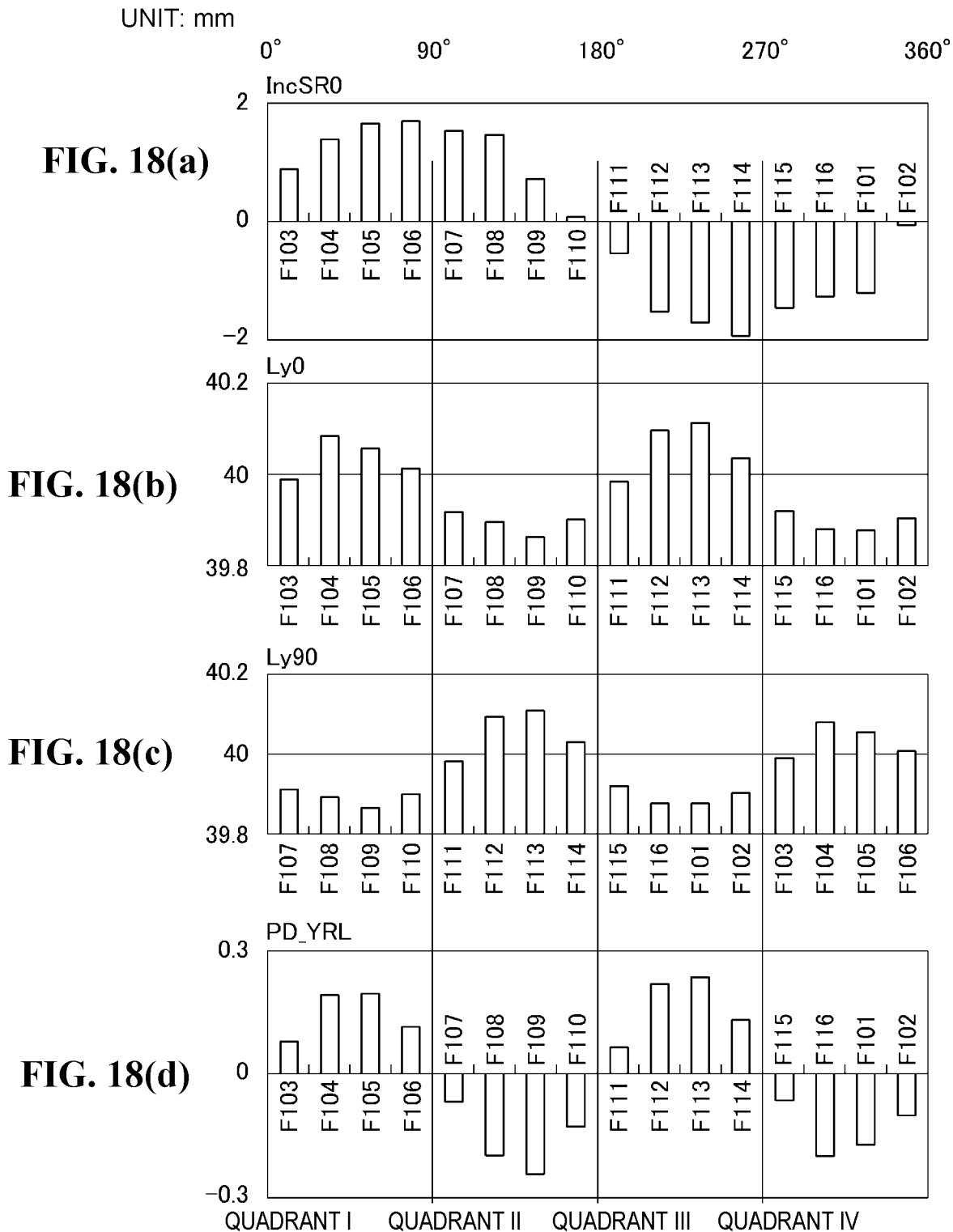

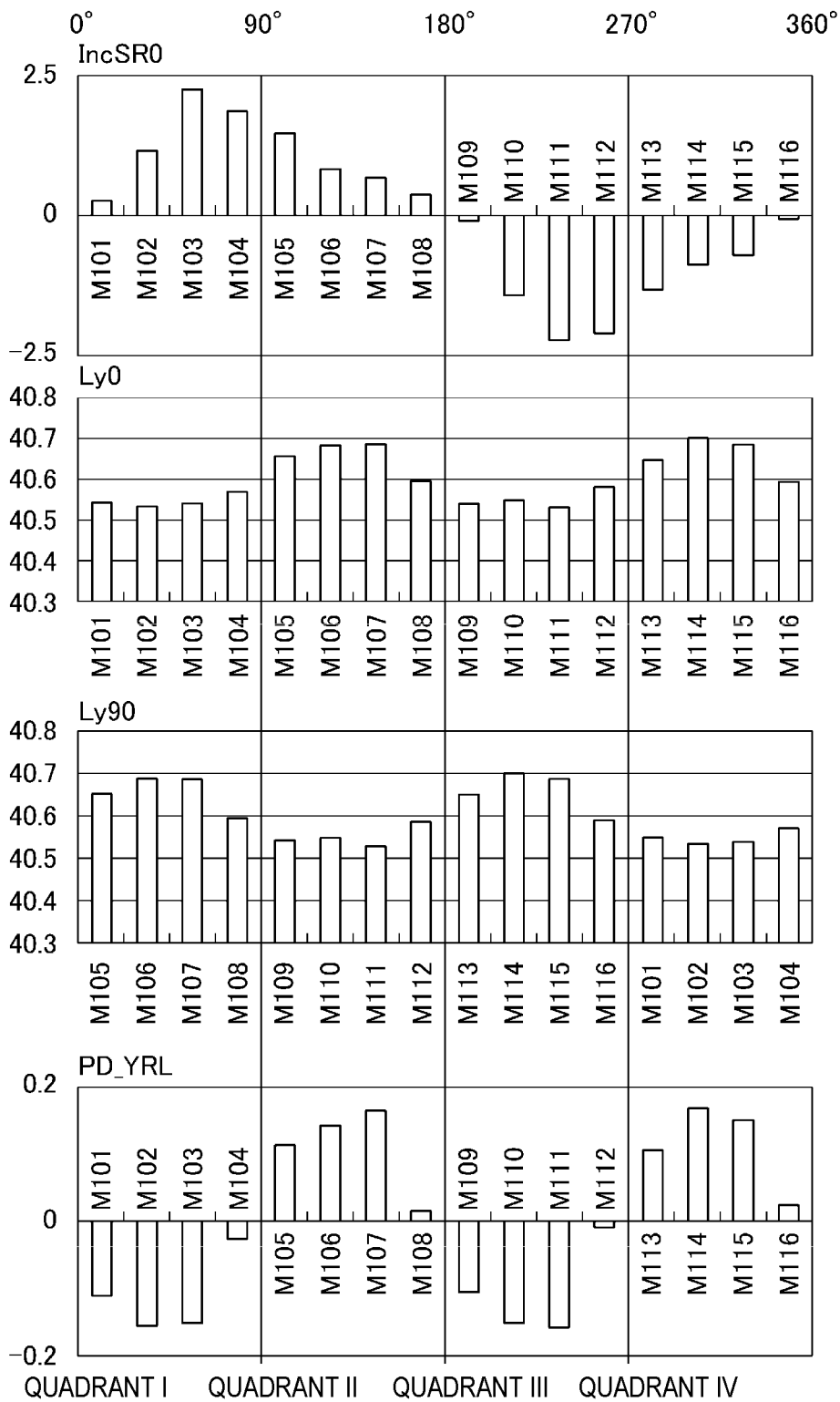

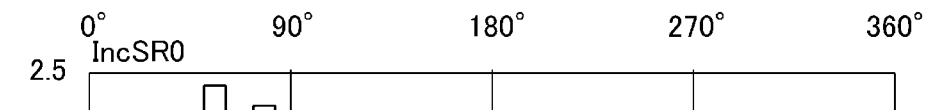
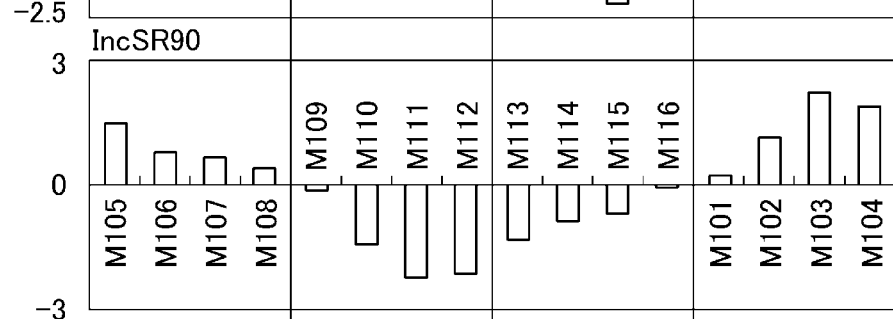
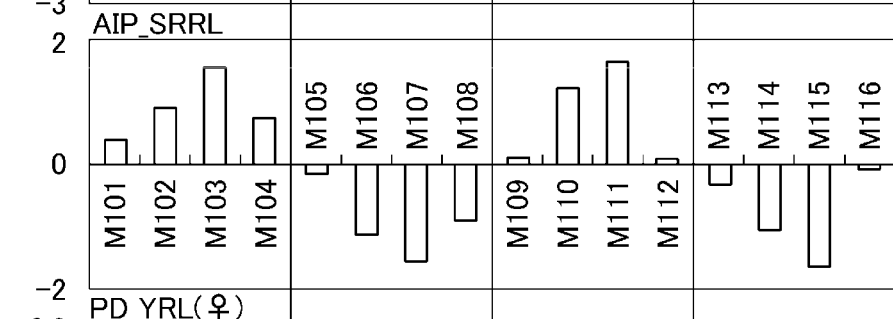
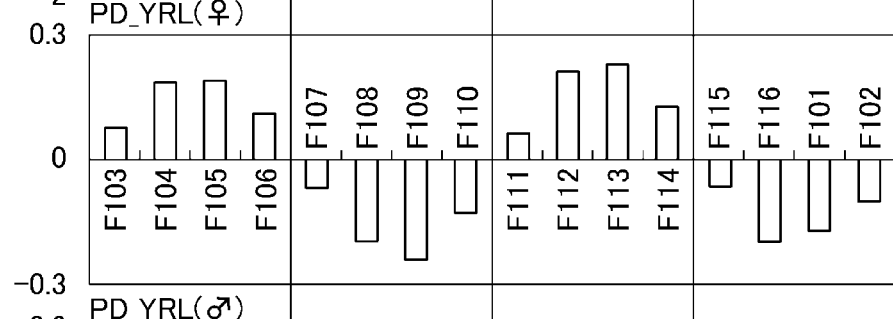
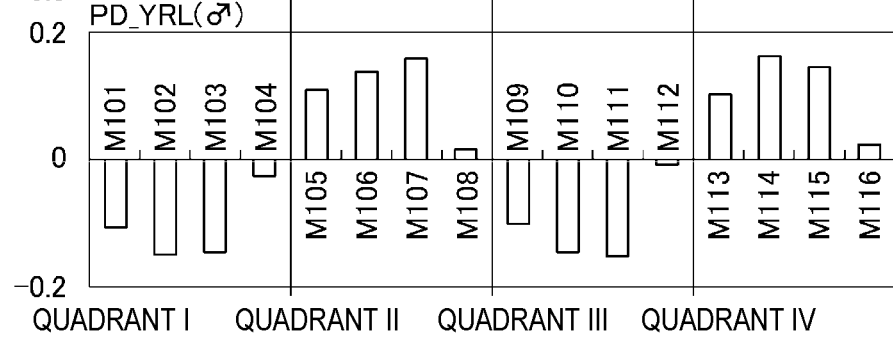
FIG. 20(a)
FIG. 20(b)
FIG. 20(c)
FIG. 20(d)
FIG. 20(e)

| Me-No | SEX | AIP_SRRL | IncSR0 | IncSR90 | PD_YRL |
|---|---|---|---|---|---|
| F103 | ♀ | IP | Right | Right | Lead |
| F104 | ♀ | IP | Right | Right | Lead |
| F105 | ♀ | IP | Right | Right | Lead |
| F106 | ♀ | IP | Right | Right | Lead |
| F111 | ♀ | IP | Left | Left | Lead |
| F112 | ♀ | IP | Left | Left | Lead |
| F113 | ♀ | IP | Left | Left | Lead |
| F114 | ♀ | IP | Left | Left | Lead |
| M101 | ♂ | IP | Right | Right | Lag |
| M102 | ♂ | IP | Right | Right | Lag |
| M103 | ♂ | IP | Right | Right | Lag |
| M104 | ♂ | IP | Right | Right | Lag |
| M109 | ♂ | IP | Left | Left | Lag |
| M110 | ♂ | IP | Left | Left | Lag |
| M111 | ♂ | IP | Left | Left | Lag |
| M112 | ♂ | IP | Left | Left | Lag |

| Me-No | SEX | AIP_SRRL | IncSR0 | IncSR90 | PD_YRL |
|---|---|---|---|---|---|
| F107 | ♀ | AP | Right | Left | Lag |
| F108 | ♀ | AP | Right | Left | Lag |
| F109 | ♀ | AP | Right | Left | Lag |
| F110 | ♀ | AP | Right | Left | Lag |
| F115 | ♀ | AP | Left | Right | Lag |
| F116 | ♀ | AP | Left | Right | Lag |
| F101 | ♀ | AP | Left | Right | Lag |
| F102 | ♀ | AP | Left | Right | Lag |
| M105 | ♂ | AP | Right | Left | Lead |
| M106 | ♂ | AP | Right | Left | Lead |
| M107 | ♂ | AP | Right | Left | Lead |
| M108 | ♂ | AP | Right | Left | Lead |
| M113 | ♂ | AP | Left | Right | Lead |
| M114 | ♂ | AP | Left | Right | Lead |
| M115 | ♂ | AP | Left | Right | Lead |
| M116 | ♂ | AP | Left | Right | Lead |

FIG. 21

| Egg-No | SEX | SGPT | AIP_SRRL | TLMC45 | AIP_XRC | PD_YRL |
|---|---|---|---|---|---|---|
| W4743 | ♀ | SGS | IP | Left | IP | Lag |
| W3691 | ♀ | SGS | IP | Left | IP | Lag |
| W4730 | ♂ | SGS | IP | Left | IP | Lead |

FIG. 22(a)

| Egg-No | SEX | SGPT | AIP_SRRL | TLMC45 | AIP_XRC | PD_YRL |
|---|---|---|---|---|---|---|
| W4709 | ♀ | SGS | IP | Left | AP | Lead |
| W3607 | ♀ | SGS | IP | Left | AP | Lead |
| W4643 | ♂ | SGS | IP | Left | AP | Lag |
| W3679 | ♂ | SGS | IP | Left | AP | Lag |

FIG. 22(b)

| Egg-No | SEX | SGPT | AIP_SRRL | TLMC45 | PD_BLARL | PD_YRL |
|---|---|---|---|---|---|---|
| W4737 | ♀ | SGS | IP | Right | Lead | Lag |
| W3635 | ♀ | SGS | IP | Right | Lead | Lag |
| W4749 | ♂ | SGS | IP | Right | Lead | Lead |
| W3685 | ♂ | SGS | IP | Right | Lead | Lead |

FIG. 22(c)

| Egg-No | SEX | SGPT | AIP_SRRL | TLMC45 | PD_BLARL | PD_YRL |
|---|---|---|---|---|---|---|
| W4307 | ♀ | SGS | IP | Right | Lag | Lead |
| W4325 | ♀ | SGS | IP | Right | Lag | Lead |
| W3617 | ♀ | SGS | IP | Right | Lag | Lag |
| W3626 | ♀ | SGS | IP | Right | Lag | Lead |
| W4717 | ♂ | SGS | IP | Right | Lag | Lag |
| W3628 | ♂ | SGS | IP | Right | Lag | Lag |

FIG. 22(d)

| Egg-No | SEX | SGPT | AIP_SRRL | IncSR0 | IncSR90 | PD_F45FB | PD_TRTCL | PD_YRL |
|---|---|---|---|---|---|---|---|---|
| W3037 | ♀ | SGS | AP | Left | Right | Lead | Lead | Lag |
| W4340 | ♀ | SGS | AP | Left | Right | Lead | Lead | Lag |
| W4317 | ♂ | SGS | AP | Left | Right | Lead | Lag | Lead |
| W4334 | ♂ | SGS | AP | Left | Right | Lead | Lag | Lead |
| W4735 | ♂ | SGS | AP | Left | Right | Lead | Lag | Lead |
| W3618 | ♂ | SGS | AP | Left | Right | Lead | Lag | Lead |

FIG. 23(a)

| Egg-No | SEX | SGPT | AIP_SRRL | IncSR0 | IncSR90 | PD_F45FB | PD_TRTCL | PD_YRL |
|---|---|---|---|---|---|---|---|---|
| W4745 | ♀ | SGS | AP | Left | Right | Lag | Lag | Lead |
| W3640 | ♀ | SGS | AP | Left | Right | Lag | Lag | Lead |
| W3675 | ♀ | SGS | AP | Left | Right | Lag | Lag | Lead |
| W4722 | ♂ | SGS | AP | Left | Right | Lag | Lead | Lag |

FIG. 23(b)

| Egg-No | SEX | SGPT | AIP_SRRL | IncSR0 | IncSR90 | PD_BLARL | PD_TRTCL | PD_YRL |
|---|---|---|---|---|---|---|---|---|
| W3039 | ♀ | SGS | AP | Right | Left | Lead | Lead | Lag |
| W4301 | ♀ | SGS | AP | Right | Left | Lead | Lead | Lag |
| W3657 | ♂ | SGS | AP | Right | Left | Lead | Lead | Lead |

FIG. 23(c)

| Egg-No | SEX | SGPT | AIP_SRRL | IncSR0 | IncSR90 | PD_BLARL | PD_TRTCL | PD_YRL |
|---|---|---|---|---|---|---|---|---|
| W3008 | ♀ | SGS | AP | Right | Left | Lead | Lag | Lead |
| W3636 | ♀ | SGS | AP | Right | Left | Lead | Lag | Lead |
| W3681 | ♀ | SGS | AP | Right | Left | Lead | Lag | Lead |

FIG. 23(d)

| Egg-No | SEX | SGPT | AIP_SRRL | IncSR0 | IncSR90 | PD_BLARL | PD_TRTCL | PD_YRL |
|---|---|---|---|---|---|---|---|---|
| W3633 | ♀ | SGS | AP | Right | Left | Lag | Lead | Lead |
| W3004 | ♂ | SGS | AP | Right | Left | Lag | Lead | Lag |
| W3014 | ♂ | SGS | AP | Right | Left | Lag | Lead | Lag |

FIG. 23(e)

| Egg-No | SEX | SGPT | AIP_SRRL | IncSR0 | IncSR90 | PD_BLARL | PD_TRTCL | PD_YRL |
|---|---|---|---|---|---|---|---|---|
| W4321 | ♀ | SGS | AP | Right | Left | Lag | Lag | Lag |
| W4723 | ♀ | SGS | AP | Right | Left | Lag | Lag | Lag |
| W4734 | ♀ | SGS | AP | Right | Left | Lag | Lag | Lead |
| W3614 | ♀ | SGS | AP | Right | Left | Lag | Lag | Lag |
| W4304 | ♂ | SGS | AP | Right | Left | Lag | Lag | Lead |

FIG. 23 (f)

SEX IDENTIFICATION DEVICE FOR FERTILIZED EGGS, SEX IDENTIFICATION METHOD FOR FERTILIZED EGGS, AND PROGRAM

CROSS-REFERENCE TO RELATED APPLICATION

This is a U.S. national phase application under 35 USC 371 of International Application PCT/JP2019/043191 (not published in English), filed Nov. 5, 2019.

TECHNICAL FIELD

The present invention relates to a technique for discriminating whether a fertilized egg is female or male.

BACKGROUND ART

Conventionally, for sexing of a fertilized bird egg, typically, a fertilized chicken egg (hereinafter also referred to simply as an egg), an approach based on observation of an egg shape (a shape of the shell of the egg) such as a swell of the head and thinness is proposed. However, sexing by the approach has not been practically used because, when the egg shape changes due to individual parent hens and breeding environments, a female/male discrimination criterion itself varies, and sexing becomes difficult. Hereinafter, a dull end side and a sharp end side (a tip end side) of a chicken egg on a long axis will be referred to as a head and a tail, respectively; and a size (a length dimension) on the long axis and a size on a short axis orthogonal to the long axis will be referred to as a long radial and a short radial, respectively.

Conventionally, an approach of sexing of a fertilized egg based on images obtained by photographing its external shape (the contour of the shell) with a plurality of cameras has been proposed. For example, Patent Literature 1 discloses a sexing approach paying attention to the fact that a phase difference obtained by calculating a difference between pieces of image data obtained by photographing area distortions that are latent in the contour of a fertilized egg (a limit cycle) at angles of 0 degrees and 90 degrees on the short radial differs between female and male eggs.

CITATION LIST

Patent Literature

Patent Literature 1:
Japanese Patent Laid-Open No. 2011-142866

SUMMARY OF INVENTION

Technical Problem

In the sexing approach disclosed in Patent Literature 1, however, a specific approach for taking the place of the sexing rate of the current anal sexing and feather sexing through image data obtained by photographing is not sufficiently disclosed. Therefore, it is impossible to obtain a sexing rate equal to the sexing rate of the current anal sexing and feather sexing of 95% to 98%, and improvement of the sexing rate is limited.

The present invention has been made in view of the above problem, and an object of the invention is to provide a technique for performing sexing of a fertilized egg with a high sexing rate at a high speed, based on image data obtained by photographing a contour of the egg.

Solution to Problem

In order to solve the above problem, a fertilized egg sexing method according to one aspect of the present invention is a fertilized egg sexing method for making a female/male judgment according to a contour of a fertilized egg by a computer, based on image data obtained by photographing by a plurality of cameras, wherein first and second cameras are installed such that, when long and short axes of the fertilized egg are assumed as X and Y axes, and an axis perpendicular to the X and Y axes is assumed as a Z axis, optical axes are inclined at an angle of 45 degrees on one side and another side on the Y axis relative to the Z axis above a two-dimensional plane defined by the X and Y axes, and both of the optical axes on the one side and the other side intersect with the Y axis at a center of the fertilized egg existing on the two-dimensional plane; and the fertilized egg sexing method includes: extracting the contour based on image data obtained by photographing the fertilized egg at different angles; calculating a short radial from the contour; calculating a short radial phase difference, which is a difference between the short radial by photographing by the first camera at an angle of 0 degrees and the short radial by photographing by the second camera at an angle of 90 degrees; calculating a logical product of inclinations of the short radials obtained by the photographing by the first camera at the angle of 0 degrees and the photographing by the second camera at the angle of 90 degrees; and making the female/male judgment using the short radial phase difference and the logical product.

A fertilized egg sexing apparatus according to another aspect of the present invention is a fertilized egg sexing apparatus for making a female/male judgment according to a contour of a fertilized egg, the fertilized egg sexing apparatus including: first and second cameras installed such that, when long and short axes of the fertilized egg are assumed as X and Y axes, and an axis perpendicular to the X and Y axes is assumed as a Z axis, optical axes are inclined at an angle of 45 degrees on one side and another side on the Y axis relative to the Z axis above a two-dimensional plane defined by the X and Y axes, and both of the optical axes on the one side and the other side intersect with the Y axis at a center of the fertilized egg existing on the two-dimensional plane; and a control unit extracting the contour based on image data obtained by photographing the fertilized egg at different angles, calculating a short radial from the contour, calculating a short radial phase difference, which is a difference between the short radial by photographing by the first camera at an angle of 0 degrees and the short radial by photographing by the second camera at an angle of 90 degrees, calculating a logical product of inclinations of the short radials obtained by the photographing by the first camera at the angle of 0 degrees and the photographing by the second camera at the angle of 90 degrees, and making the female/male judgment using the short radial phase difference and the logical product.

A program according to another aspect of the present invention is a program for making a female/male judgment of a fertilized egg based on image data obtained by photographing by first and second cameras arranged such that, when long and short axes of the fertilized egg are assumed as X and Y axes, and an axis perpendicular to the X and Y axes is assumed as a Z axis, optical axes are inclined at an angle of 45 degrees on one side and another side on the Y axis relative to the Z axis above a two-dimensional plane defined by the X and Y axes, and both of the optical axes on the one side and the other side intersect with the Y axis at a center of the fertilized egg existing on the two-dimensional plane, wherein the program causes a computer to function as a control unit extracting a contour based on image data obtained by photographing the fertilized egg at different angles, calculating a short radial from the contour, calculating a short radial phase difference, which is a difference between the short radial by photographing by the first camera at an angle of 0 degrees and the short radial by photographing by the second camera at an angle of 90 degrees, calculating a logical product of inclinations of the short radials obtained by the photographing by the first camera at the angle of 0 degrees and the photographing by the second camera at the angle of 90 degrees, and making the female/male judgment using the short radial phase difference and the logical product.

Advantageous Effect of Invention

According to the present invention, it is possible to provide a technique for performing sexing of a fertilized egg with a high sexing rate at a high speed, based on image data obtained by photographing a contour of the egg.

BRIEF DESCRIPTION OF DRAWINGS

FIG. 2 shows analysis results of image data showing sexing characteristics of fertilized eggs.

FIGS. 17(a) to 17(c) are diagrams illustrating the first viewpoint of sexing by the fertilized egg sexing apparatus according to the second embodiment of the present invention.

FIGS. 18(a) to 18(d) are diagrams illustrating a second viewpoint of sexing by the fertilized egg sexing apparatus according to the second embodiment of the present invention.

FIGS. 19(a) to 19(d) are diagrams illustrating the second viewpoint of sexing by the fertilized egg sexing apparatus according to the second embodiment of the present invention.

FIGS. 20(a) to 20(e) are diagrams illustrating a third viewpoint of sexing by the fertilized egg sexing apparatus according to the second embodiment of the present invention.

FIG. 21 is a diagram illustrating a fourth viewpoint of sexing by the fertilized egg sexing apparatus according to the second embodiment of the present invention.

FIGS. 22(a) to 22(d) are diagrams showing analysis results by the fertilized egg sexing apparatus according to the second embodiment of the present invention.

FIGS. 23(a) to 23(f) are diagrams showing analysis results by the fertilized egg sexing apparatus according to the second embodiment of the present invention.

DESCRIPTION OF EMBODIMENTS

Figure 1A:
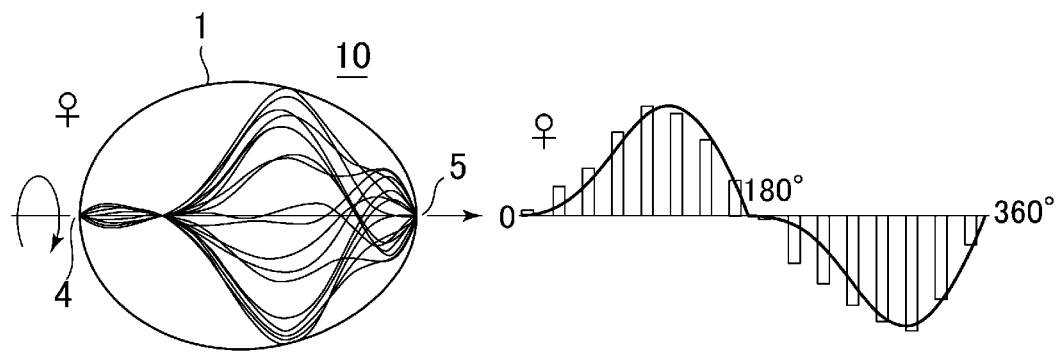
FIGS. 1(a) and 1(b) are diagrams illustrating that differences between the contour of an egg and contour distortions of the egg are different depending on whether the egg is a female egg or a male egg, which is a viewpoint of sexing by a fertilized egg sexing apparatus according to a first embodiment of the present invention.

An embodiment of the present invention will be described below with reference to drawings.

First Embodiment

A first embodiment of the present invention is, for example, characterized in the following.

(a-1) Three-dimensional changes in a contour vector average value or a photographed angular difference in contour area due to contour distortions obtained by photographing the contour of an inspection target fertilized egg at different angles reveal a latent minute spiral shape, which occurs by the egg rotatingly coming out of a parent hen. The inventor of the present application paid attention to the fact that the rotation direction is opposite depending on whether female or male. The three-dimensional characteristics of an egg shell that are different between female and male eggs can be converted to data as female and male three-dimensional characteristics. According to a fertilized egg sexing apparatus and the like according to the first embodiment of the present invention, since the data of the three-dimensional characteristics can be revealed as parameters for characterizing whether female or male, it is possible to appropriately perform sexing based on the parameters.

(a-2) The fertilized egg sexing apparatus according to the first embodiment of the present invention is configured being provided with photographing means using one or more cameras for photographing the external surface (the shell, the contour and the like) of a fertilized egg, which is an inspection target, at different angles and image processing means. As the cameras, high-resolution CCD or CMOS image sensors or the like are adopted. By photographing the external shape (the contour of the shell) of a fertilized egg with one camera at different angles or with a plurality of cameras to three-dimensionally acquire image data, and converting the image data to detailed contour data, data in which traces of the rotation as described above are revealed is obtained.

The first embodiment of the present invention will be described below in detail.

First, a detailed description will be made on a viewpoint that the fertilized egg sexing apparatus, a fertilized egg sexing method and a program according to the first embodiment of the present invention paying attention to at the time of sexing a fertilized egg while experiment data and the like are introduced.

First, with reference to FIGS. 1(a) to 1(d), it will be described that differences between the contour of an egg and contour distortions of the egg are different depending on whether the egg is a female egg (♀) or a male egg (♂), which is the viewpoint of sexing by the fertilized egg sexing apparatus according to the first embodiment of the present invention.

In the present embodiment, contour distortions are calculated from contour data extracted from images photographed while each egg 10 being rotated to the right around a long radial connecting a dull end 4 and a sharp end 5 of the egg 10 by 360 degrees in a direction indicated by an arrow in FIG. 1. FIG. 1(a) enlargingly shows a contour 1 of each egg 10 and contour distortions. FIG. 1(b) shows the contour distortions of the contour 1 calculated from camera outputs (velocity change: angular velocity) obtained by intermittently photographing each egg 10 at photographing angles from 0 to 360 degrees.

Figure 1B:
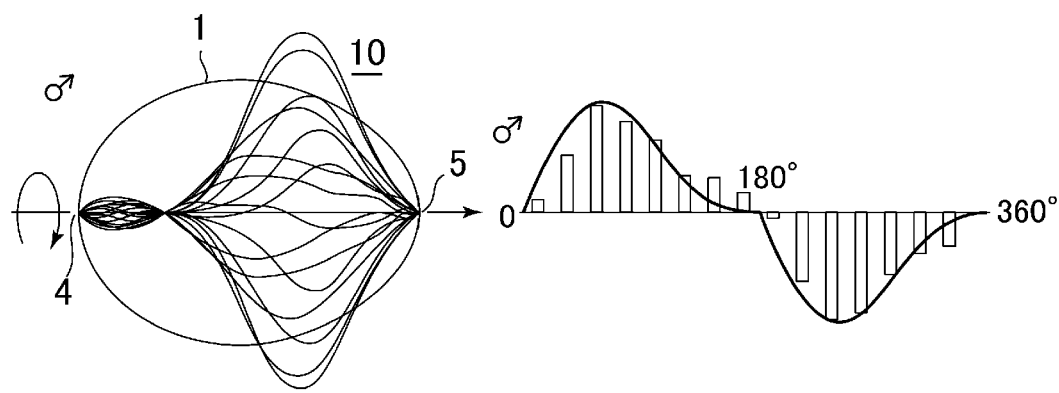

As shown in FIG. 1(b), the velocity curve pattern is different between the female and male eggs, which is caused by the fact that the rotation direction at the time of coming out of a parent hen is opposite between the female and male eggs. This characteristic can be defined as a periodic function configured with relaxation oscillations by two frequencies. Note that, as for the relaxation oscillations, the idea of the known van der Pol's equation can be applied.

Here, when a viscosity coefficient and an oscillation amplitude are indicated by γ and θ, respectively, a forced oscillation can be generally defined like the following equation:

$$\frac{d^2\theta}{dt^2} - \gamma_0 \left[1 - \frac{\theta^2}{\theta_0^2}\right] \frac{d\theta}{dt} + \varpi^2 \theta = 0 \quad \text{[Equation 1]}$$

In order to appropriately express the forced oscillation, the following are required:
To break invariance of enlargement or reduction;
To control increase in energy when γ<0; and
To enable continuous supply in order to make up for energy loss when γ<0.

It was pointed out by van der Pol for the first time that, by a mathematically simple change of causing the viscosity coefficient γ to be dependent on the oscillation amplitude 0, it is possible to give the nature as described above. When the amplitude is small, γ can be negative, and γ can be positive when the amplitude is large. The van der Pol's equation is defined by the following equation that includes a parameter ε that has been made dimensionless.

$$\frac{d^2\theta}{dt^2} - (\varepsilon - \theta^2)\frac{d\theta}{dt} + \theta = 0 \quad \varepsilon = \gamma_0/\varpi \quad \text{[Equation 2]}$$

According to the above equation, when ε is large, temporal change in the amplitude 0 shows a phenomenon in two different time scales. One is a part showing slow fluctuations, and the other is a part showing abrupt changes. This characteristic phenomenon is the relaxation oscillations described before. A motion θ(t) of a limit cycle (periodic start included in a limit set at a certain point) can be shown by a Fourier series and can be defined like the following equation no matter which mechanical quantity X(t) is taken.

$$X(t) = \sum_{n=0}^{\infty} x_n \sin(n\varpi t + \phi_n) \quad \text{[Equation 3]}$$

A velocity approximation equation is defined by the following equation:

$$V_i = \sin \omega t \pm 0.5 \sin 2\omega t \quad \text{[Equation 4]}$$

Figure 1C:
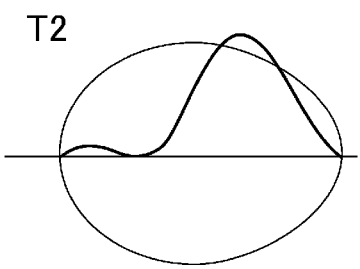
FIGS. 1(c) and 1(d) are diagrams showing the contour distortions.
Figure 1D:
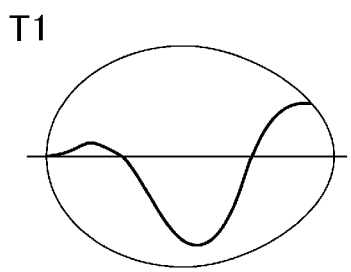

Furthermore, contour distortions as shown in FIGS. 1(c) and 1(d) are shown by the following equations:

$$LMC(T2) = \sin 0.5 \, \omega t$$

$$LMC(T1) = \sin \omega t \quad \text{[Equation 5]}$$

In FIG. 2, analysis results of image data showing sexing characteristics of the fertilized eggs are shown and described. Note that FIG. 3 shows positions (angles relative to each fertilized egg) of a camera that photographs the fertilized egg.

Figure 3:
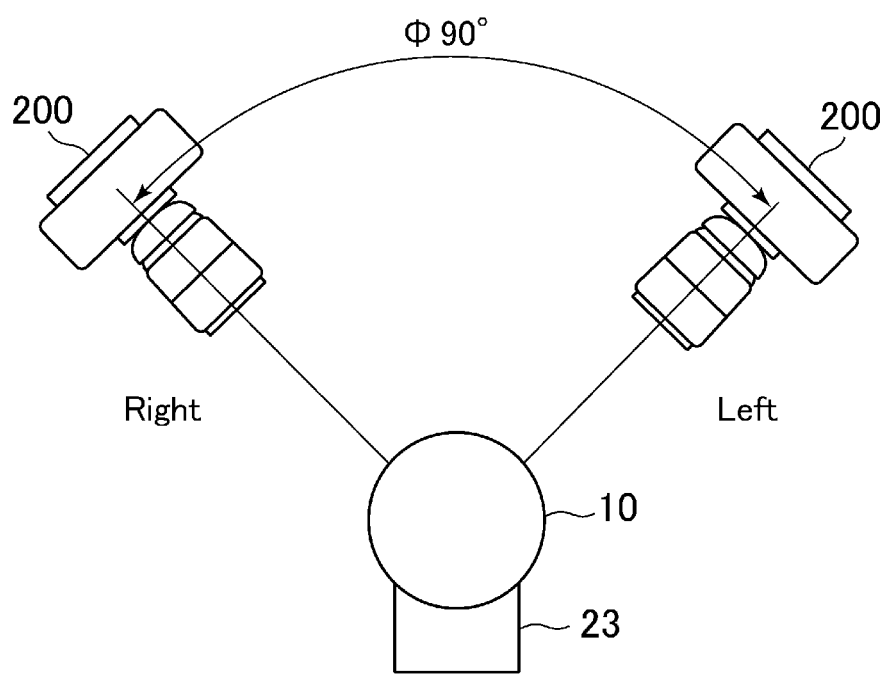
FIG. 3 is a diagram showing an installation relationship between cameras.

As shown in FIG. 3, each egg 10 is placed on a placement stand 23 such that its long axis is in a direction from this side toward the depth. A camera 200 photographs the contour of the egg at right and left positions (Right and Left) on the short axis side of the placed egg with an angular difference of 90 degrees. In more detail, the long and short axes of the fertilized egg are assumed as X and Y axes, and an axis perpendicular to the X and Y axes is assumed as a Z axis; an optical axis is inclined at an angle of 45 degrees relative to the Z axis, on each of one side and the other side on the Y axis; and the contour of the fertilized egg is photographed at positions on the one side (a photographing angle of 0 degrees) and the other side (a photographing angle of 90 degrees) with the angular difference of 90 degrees. Then, a difference between pieces of image data obtained by the photographing is determined to judge a rotation direction. By determining this rotation direction, sexing becomes possible.

In FIG. 2, Meas-No indicates a photographing number of each inspected egg; SEX indicates a result of verification by feather sexing, IncSR0 indicates an inclination direction of the short radial of the contour at the photographing angle of 0 degrees, IncSR90 indicates an inclination direction of the short radial of the contour at the photographing angle of 90 degrees, PD_YRL indicates a short radial phase difference, PD_SEAL indicates an area angular difference, PD_TRFRL indicates a contour angular difference, and PD_TRARL indicates an all contour vector angular difference. Furthermore, in each assessment field, Left and Right indicate that the short radial inclination is in a lower left direction and in a lower right direction, respectively, and Lag and Lead indicate phase lag and phase lead, respectively.

As apparent from FIG. 2, there is a possibility that differences between characteristics of the female and male eggs can be confirmed in PD_TRFRL and PD_TRARL. Note that, for PD_TRARL, there are several errors, and this is considered to be caused by photographing errors.

Figure 4A:
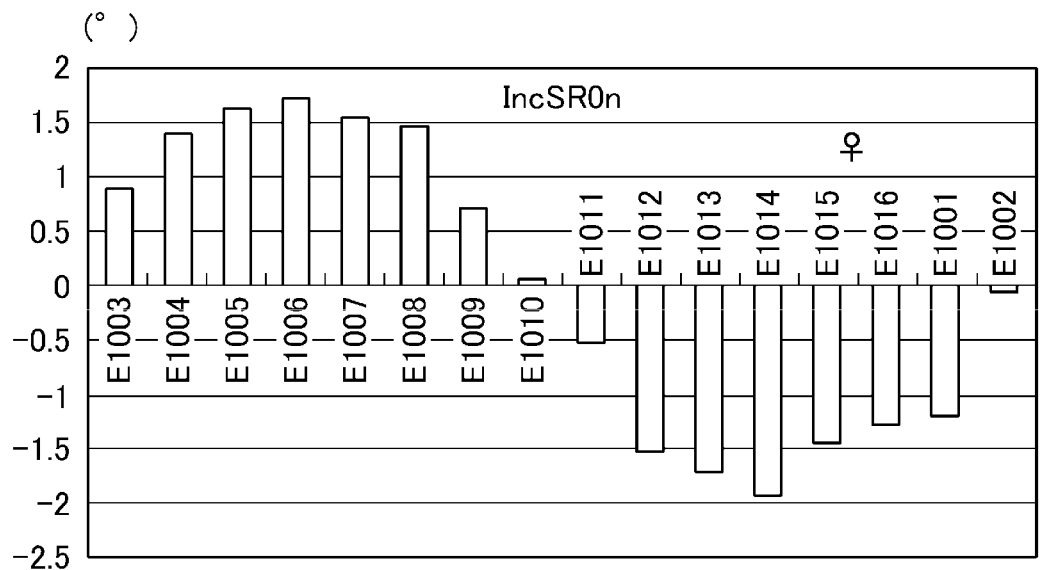
FIGS. 4(a) and 4(b) are diagrams showing changes in inclinations of short radials taken out from image data obtained by performing photographing for 360 degrees around long axes of the fertilized eggs in the right direction when seen from the dull end side.
Figure 4B:
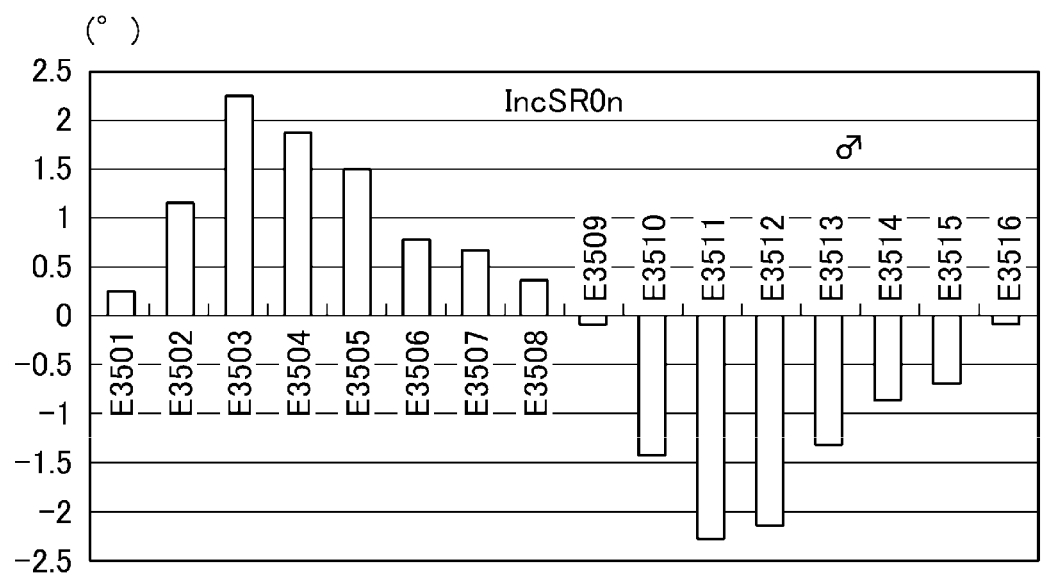

In FIGS. 4(a) and 4(b), changes in the inclination of the short radial taken out from image data obtained by performing photographing for 360 degrees around the long axes of each fertilized egg in the right direction when seen from the dull end side are shown and described. Specifically, FIG. 4(a) shows characteristics of the female egg, and FIG. 4(b) shows characteristics of the male egg. In each figure, the axis of abscissas indicates photographing numbers, and the axis of ordinates indicates amounts of inclination (°). Furthermore, on the axis of ordinates, a value larger than 0 indicates inclination to the right (right inclination), and a value smaller than 0 indicates inclination to the left (left inclination). Here, in order to make it easy to understand the description, the right inclination is set as a start point for both of the female and male eggs. As apparent from FIGS. 4(a) and 4(b), since the inclination characteristic of the short radial around the long axis is different between the female and male fertilized eggs, it becomes possible to perform sexing of a fertilized egg by calculating the inclination.

Figure 5A:
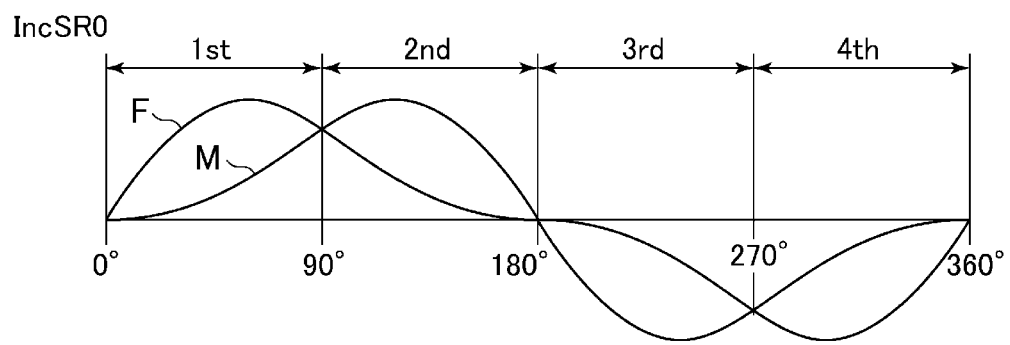
FIGS. 5(a) to 5(c) are diagrams showing angular differences of the short radial of each fertilized egg.
Figure 5B:
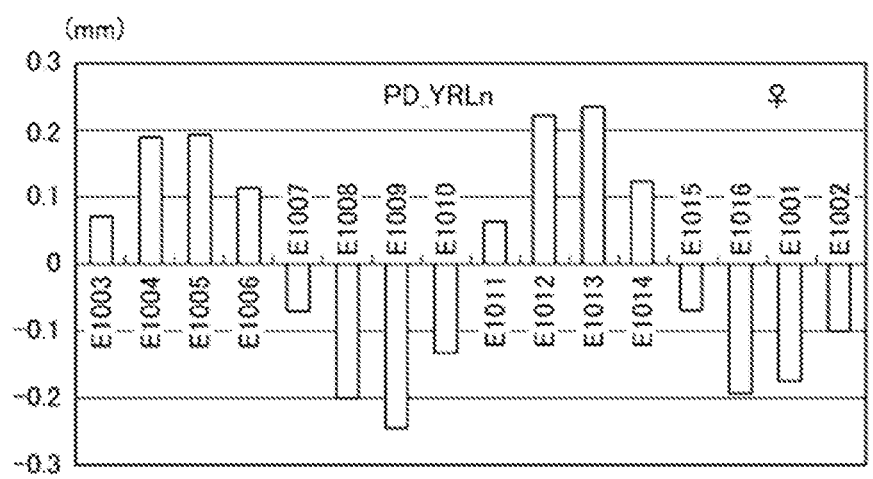
Figure 5C:
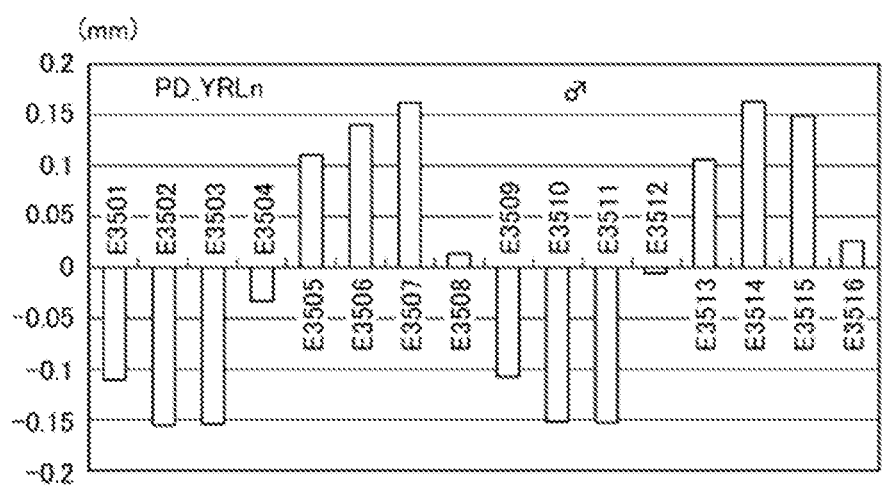

In FIG. 5(a), the changes in the inclinations of the short radials are shown and described. In FIGS. 5(b) and 5(c), phases of the short radials of each fertilized egg are shown and described. More specifically, FIG. 5(a) shows changes in inclinations IncSR0 of the short radials of the contours at the photographing angle of 0 degrees, and a region is divided in regions corresponding to 0 to 90 degrees, 90 to 180 degrees, 180 to 270 degrees, and 270 to 360 degrees. The characteristics of the female egg are indicated by a curve F, and the characteristics of the male egg is indicated by a curve M. FIG. 5(b) shows short radial phase differences PD_YRLn of the female egg, and FIG. 6(c) shows short radial phase differences PD_YRLn of the male egg. A value larger than 0 indicates a right rotation, and a value smaller than 0 indicates a left rotation. In each region, the female and male characteristics are mutually different. Therefore, it is possible to perform sexing by utilizing the short radial phase differences of a fertilized egg.

Figure 6A:
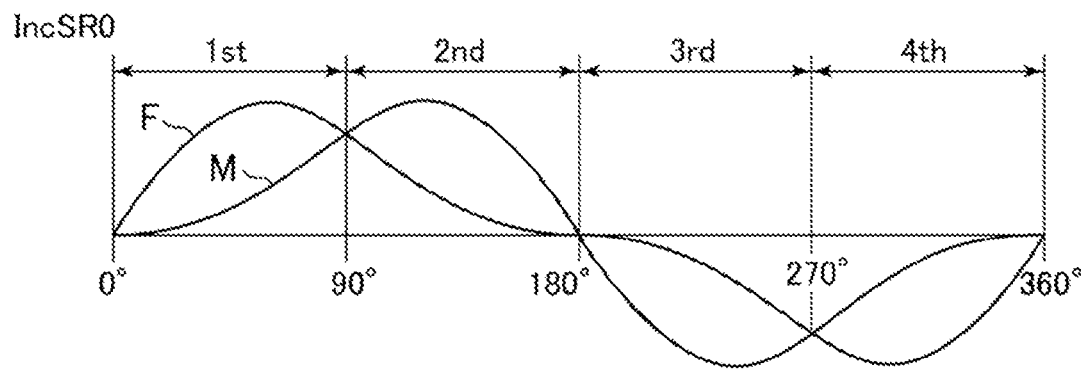
FIGS. 6(a) to 6(c) are diagrams showing angular differences of a contour area of each fertilized egg.
Figure 6B:
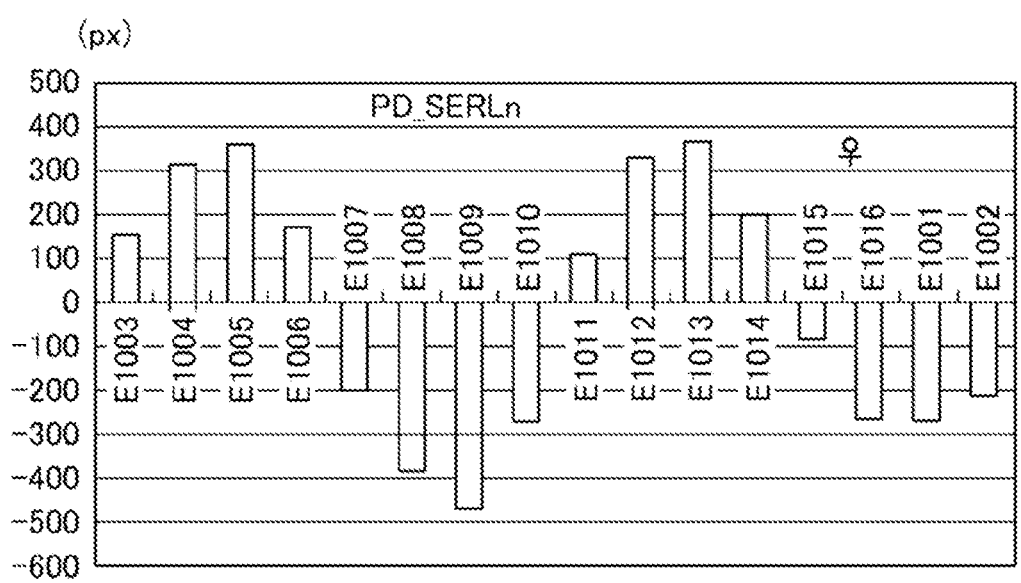
Figure 6C:
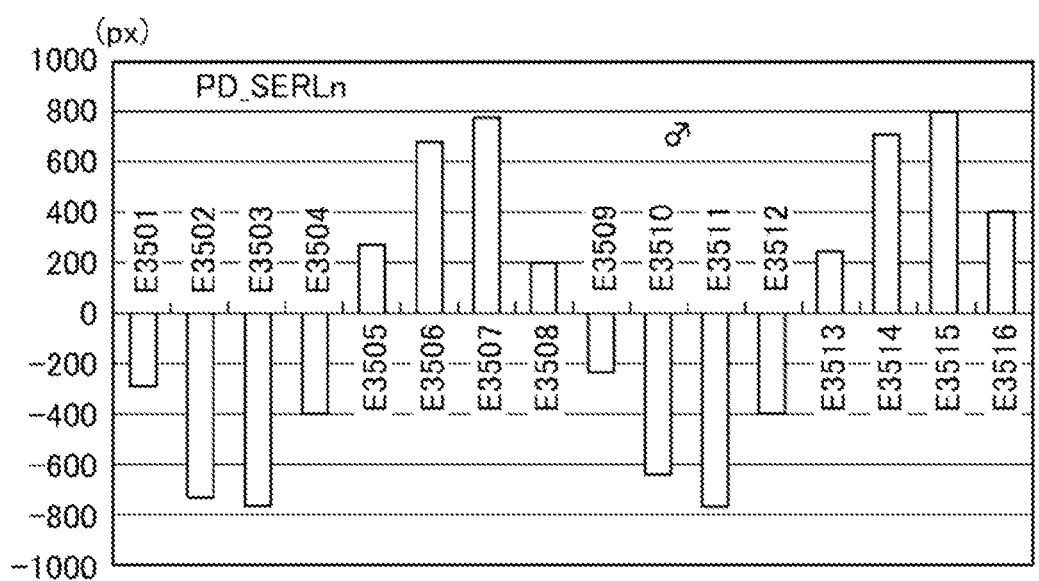

In FIG. 6(a), the changes in the inclinations of the short radials are shown and described; and, in FIGS. 6(b) and 6(c), angular differences among contour areas of the fertilized eggs are shown and described. More specifically, FIG. 6(a) shows changes in the inclinations IncSR0 of the short radials of the contours at the photographing angle of 0 degrees, and a region is divided in regions corresponding to 0 to 90 degrees, 90 to 180 degrees, 180 to 270 degrees, and 270 to 360 degrees. The characteristics of the female egg are indicated by a curve F, and the characteristics of the male egg is indicated by a curve M. FIG. 6(b) shows area angular differences PD_SERLn of the female egg, and FIG. 6(c) shows area angular differences PD_SERLn of the male egg. Differences appear between characteristics of the area angular differences PD_SERLn of the female and male eggs in the same phases as the short radial phase differences. Therefore, it is possible to perform sexing by utilizing the angular differences of the contour area of a fertilized egg.

Figure 7A:
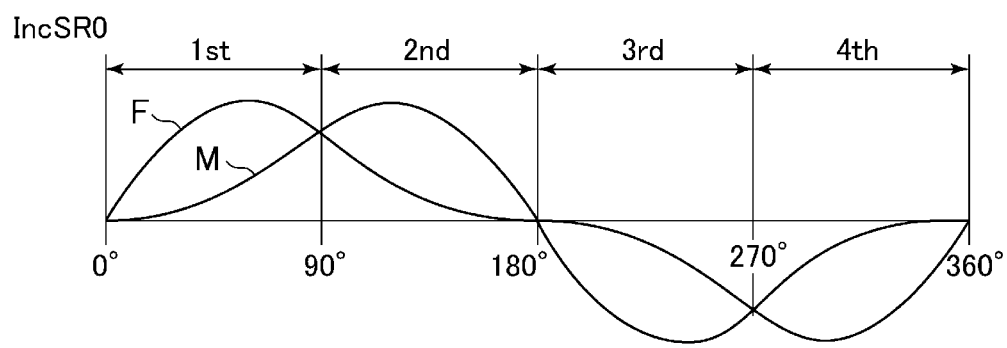
FIGS. 7(a) to 7(c) are diagrams showing angular differences of an integrated value of a contour vector from the head top of the contour of each fertilized egg to 54 degrees.
Figure 7B:
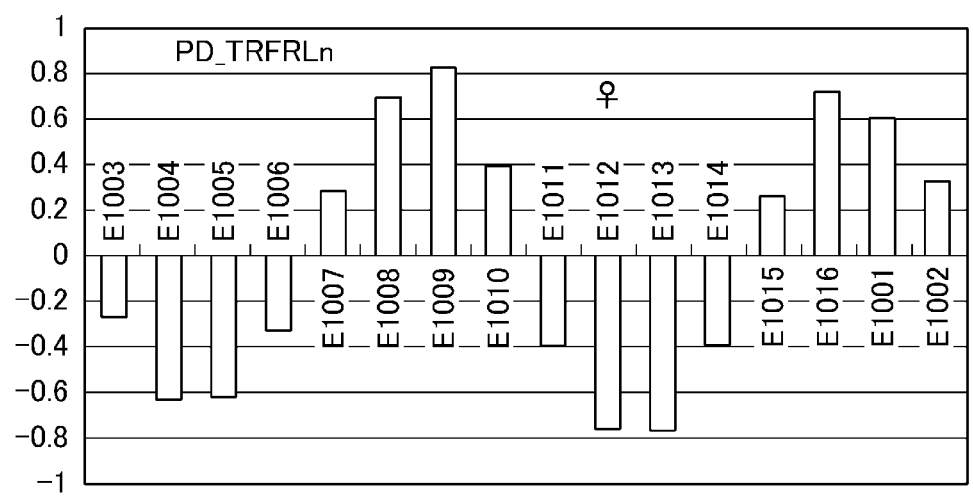
Figure 7C:
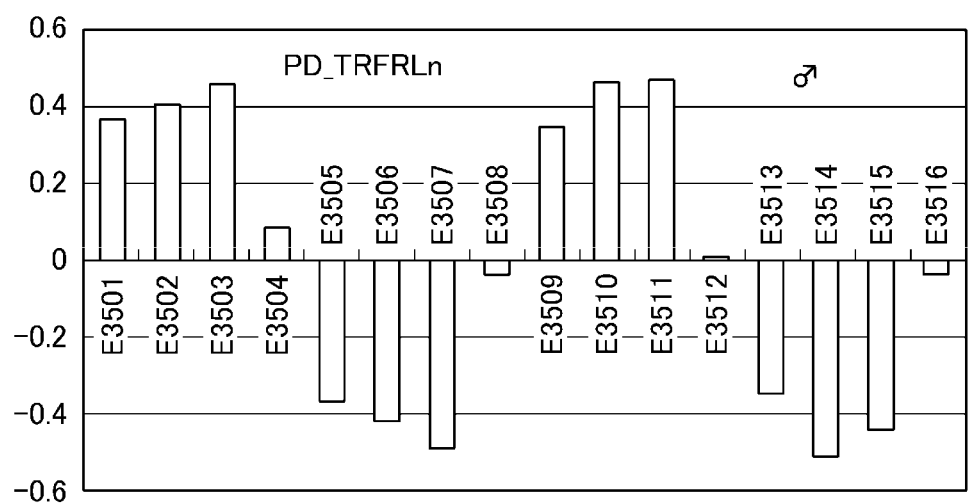

In FIG. 7(a), the changes in the inclinations of the short radials are shown and described; and, in FIGS. 7(b) and 7(c), angular differences among integrated values of contour vectors from the head top of the contour of each fertilized egg to predetermined angles are shown and described. More specifically, FIG. 7(a) shows changes in the inclination IncSR0 of the short radial of the contour at the photographing angle of 0 degrees. A region is divided in regions corresponding to 0 to 90 degrees, 90 to 180 degrees, 180 to 270 degrees, and 270 to 360 degrees. The characteristics of the female egg are indicated by a curve F, and the characteristics of the male egg are indicated by a curve M. FIGS. 7(b) and 7(c) show the angular differences PD_TRFRL of the contours from the angle of 0 degrees to the angle of 45 degrees (referred to as contours F) for the female and male eggs, respectively. Each angular difference PD_TRFRL is obtained by, after converting the contour to vector values, determining average values of the left and right values and calculating an angular difference at the angle of 90 degrees. As apparent from FIGS. 7(a) to 7(c), the characteristics are opposite to those of the short radial phase differences and the area angular differences described before, but there is regularity. Therefore, it is possible to perform sexing by utilizing the angular differences PD_TRFRL of the contour F of a fertilized egg.

Thus, in three-dimensional changes in a contour vector average value or a contour area angular difference due to contour distortions obtained by photographing the contour of an inspection target fertilized egg at different angles, a structurally non-linear characteristic showing a rotation that occurs when the egg comes out of a parent hen appears. By performing sexing based on this non-linearity, each of three-dimensional female and male characteristics, which exists on the contours of a fertilized egg can be converted to data, and appropriate fertilized egg sexing becomes possible by the data indicating the three-dimensional characteristics.

Figure 8A:
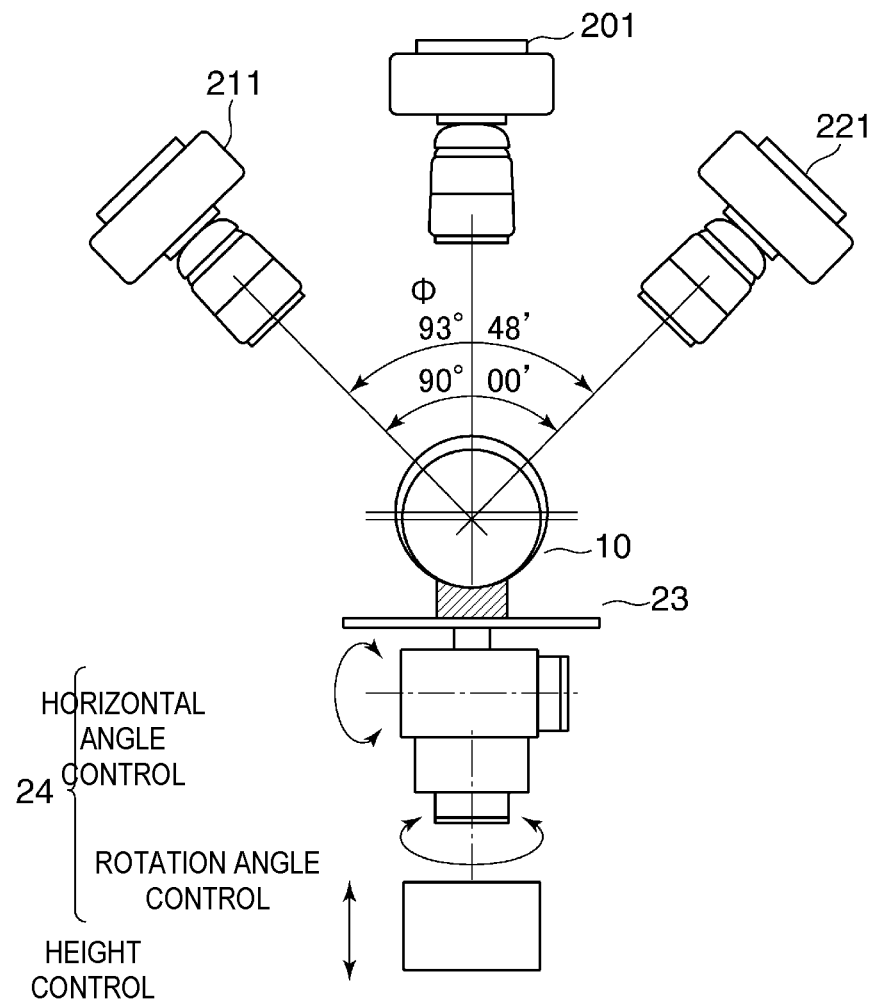
FIGS. 8(a) to 8(c) are diagrams showing a configuration of a photographing system which is a part of the fertilized egg sexing apparatus.
Figure 8B:
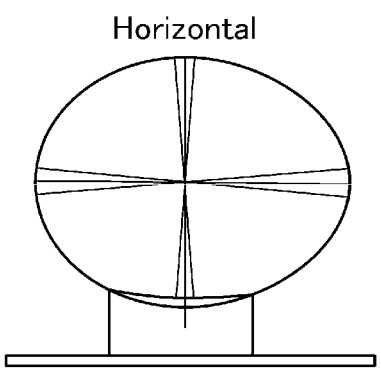
Figure 8C:
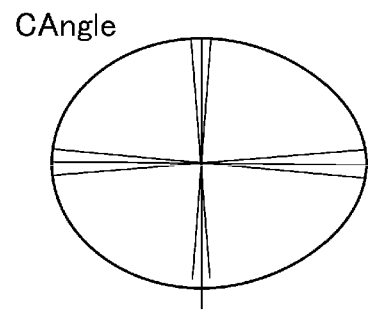

Here, in FIG. 8, a configuration of a photographing system, which is a part of the fertilized egg sexing apparatus, is shown and described. FIG. 8(a) is a schematic diagram of the photographing system; FIG. 8(b) shows a procedure of horizontal position adjustment of a fertilized egg to be a photographing target; and FIG. 8(c) shows the procedure of the horizontal position adjustment.

As shown in FIG. 8, the configuration of the photographing system includes three cameras 201, 211 and 221 arranged so that photographing at different photographing angles is possible. The long and short axes of the fertilized egg are assumed as X and Y axes, and an axis perpendicular to the X and Y axes is assumed as a Z axis; the camera 201 (a center camera) is installed above a two-dimensional plane defined by the X and Y axes and above the Z axis of the fertilized egg, which is a part where the X and Y axes intersect; and the camera 211 (a left camera) and the camera 221 (a right camera) are installed such that optical axes are inclined at the angle of 45 degrees on one side and the other side on the Y axis relative to the Z axis above the two-dimensional plane, and both of the optical axes on the one side and the other side intersect with the Y axis at the center of the fertilized egg existing on the two-dimensional plane. In this example, photographing by the camera 211 (the left camera) is referred to as photographing at an angle of 0 degrees, and photographing by the camera 221 (the right camera) is referred to as photographing at an angle of 90 degrees.

The placement stand 23 on which the inspection target egg 10 is placed is driven by a three-axis control unit 24 that is responsible for horizontal angle control, rotation angle control and height control. The egg 10 is placed on the placement stand 23 with its long radial in a direction perpendicular to the surface of FIG. 8. The horizontal angle, rotation angle and height of the placement stand 23 are controlled by the three-axis control unit 24 according to the attitude and size of the fertilized egg so that the center of the long axis (the long radial) corresponds to the intersection of the optical axes of the three cameras 201, 211 and 221. Generally, the camera 201 is installed such that its optical axis corresponds to the vertical line (the Z axis perpendicular to the X-Y axis plane of the placement stand 23).

In general, it is known that the egg size changes by almost 20% during a period from the time a parent hen begins to lay eggs to the time the hen becomes a spent hen. The center of an egg placed on the placement stand 23 changes due to the change. Since the position of the long axis of an egg changes on the horizontal plane and on the vertical line, accompanying the change of the center, the contour of the egg is not correctly photographed. As a result, accuracy of angular differences to capture a rotation direction of the egg deteriorates, and accurate image data cannot be obtained, which influences a sexing rate.

Therefore, in the present embodiment, the three-axis control unit 24 that performs the horizontal angle control for adjusting the X-Y axes (the horizontal plane, the two-dimensional plane) of the placement stand 23, the rotation angle control for controlling the orientation angle of the long axis and the height control is provided in order to solve the above problem. In FIG. 8, accompanying increase in the size of the egg, the center of the egg changes along the vertical line (the Z axis) from the intersection of the optical axes of the cameras 211 and 221 and moves upward. This change corresponds to an upward shift in the X axis direction from a position at the angle of 90 degrees at which photographing should be performed by the left and right cameras 211 and 221. Therefore, the three-axis control unit 24 drive-controls the placement stand 23 so as to adjust a point at which the optical axes of the left and right cameras 211 and 221 intersect to the long axis of the egg. Note that the three-axis control unit 24 may adopt a servo-control system.

Photographing operation by such a configuration is as follows. First, an inspection target egg is placed on the placement stand 23, and the three-axis control unit 24 performs servo-control so that the long axis of the egg seen by the camera 201 is parallel to the X axis, horizontal (one of horizontal and vertical scan directions; here, the horizontal direction is assumed to be the X axis) of the camera. The same goes for a rotation angle CAngle.

Then, the short radial (the short axis size, the width) of the egg is calculated based on image data obtained by photographing by the camera 201, and height adjustment (Z axis adjustment) is performed so that a fixed value set in advance is obtained. Similarly, a horizontal angle is adjusted based on the image data obtained by photographing by the camera 201, and long axes of image data obtained by photographing by the cameras 211 and 221 are caused to correspond to a long axis of the image data obtained by photographing by the camera 201. In a state in which all are adjusted, three-sided image photographing by the cameras 201, 211 and 221 is performed.

Here, the center of the contour of a fertilized egg and a structure seen on a two-dimensional plane with the short radial as a center will be described with reference to FIGS. 9(*a*) to 9(*c*).

Figure 9A:
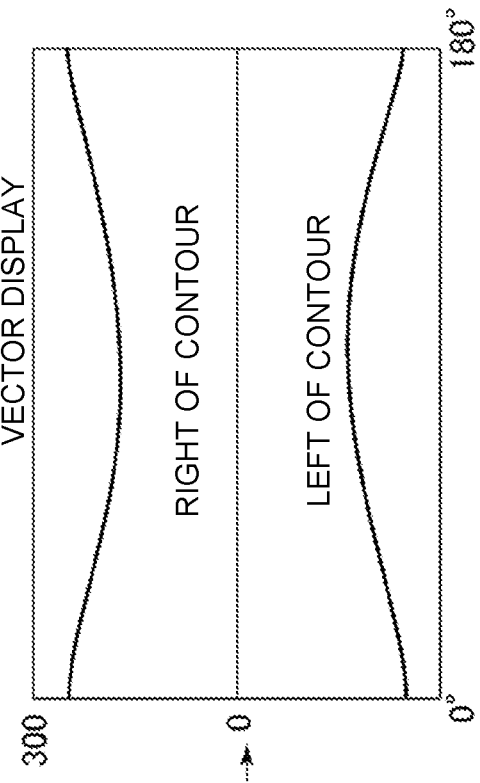
FIGS. 9(a) to 9(c) are diagrams illustrating a center of a contour of a fertilized egg, and a structure seen on a two-dimensional plane with a short radial as a center.
Figure 9B:
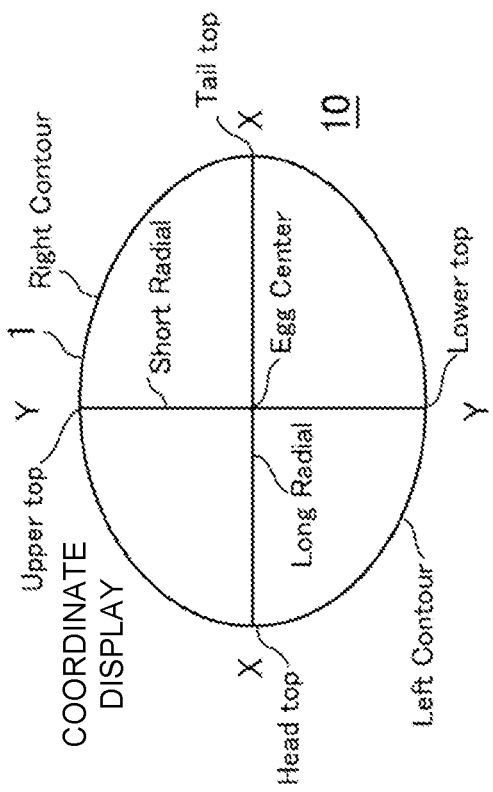
Figure 9C:
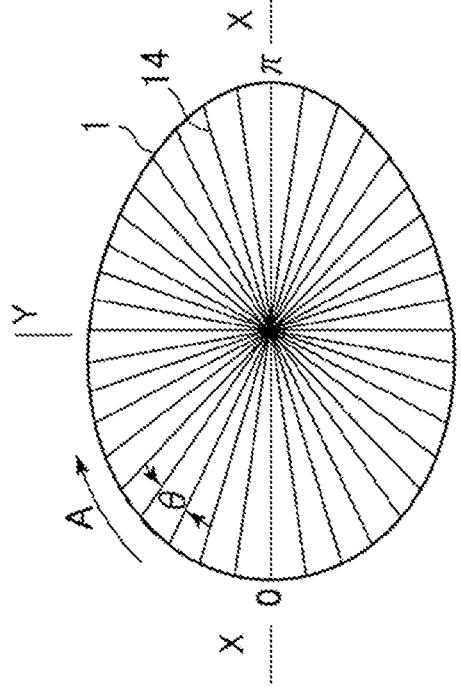

FIG. 9(*a*) shows length changes (vector changes) of lines (line segments) 14, which are radially drawn from the center of an egg (an intersection between the X and Y axes) toward the shell at predetermined angles θ at the time when the lines (line segments) 14 are moved in a direction of an arrow A. FIG. 9(*b*) shows vector changes of the right of the contour (a curved line on the upper side) and the left of the contour (a curved line on the lower side) in a case where the contour of the egg is seen at 0 degrees to 180 degrees. FIG. 9(*c*) shows coordinate display for applying the vector changes to the contour of the egg.

As shown in FIG. 9(*c*), on the contour 1 of the egg, a line connecting a head top which is a dull end and a tail top which is a sharp end is referred to as a long radial, a line connecting an upper top which is a right top of a short axis and a lower top is referred to as a short radial, a contour on the upper top side is referred to as a right contour, and a contour on the lower top side is referred to as a left contour in the present embodiment. It goes without saying that, because of individual differences, the center of the short radial of an egg does not necessarily correspond to the center of the long radial (an egg center).

A configuration and operation of the fertilized egg sexing apparatus according to the first embodiment of the present invention, which adopts the sexing viewpoint described before, will be described below in detail.

Figure 10A:
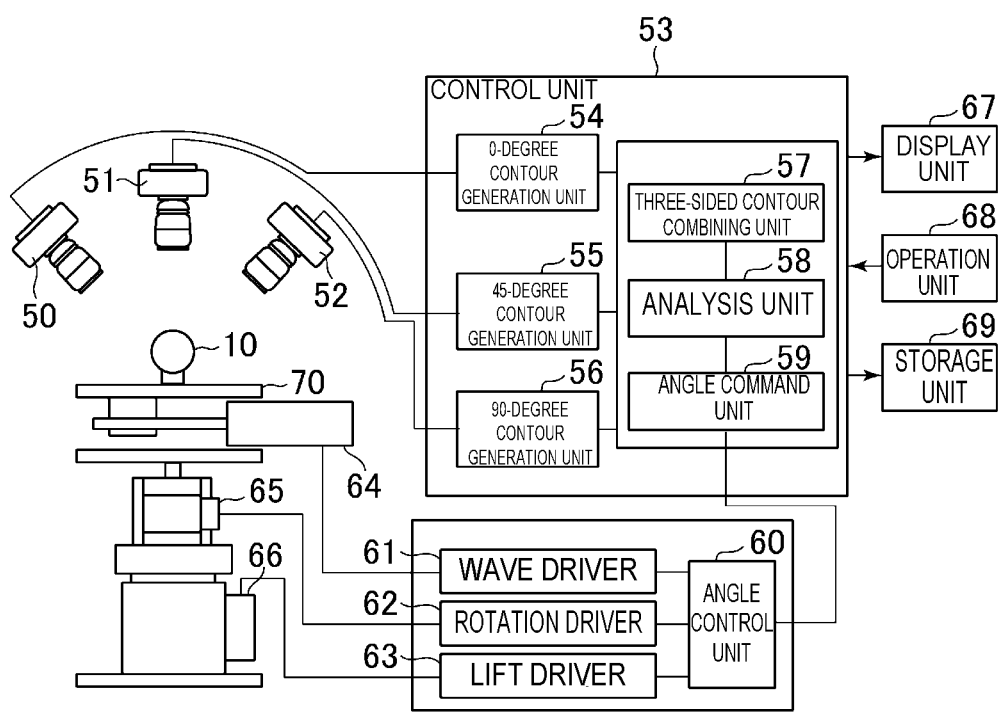
FIGS. 10(a) and 10(b) are diagrams showing a configuration of a control system of the fertilized egg sexing apparatus according to the first embodiment of the present invention.
Figure 10B:
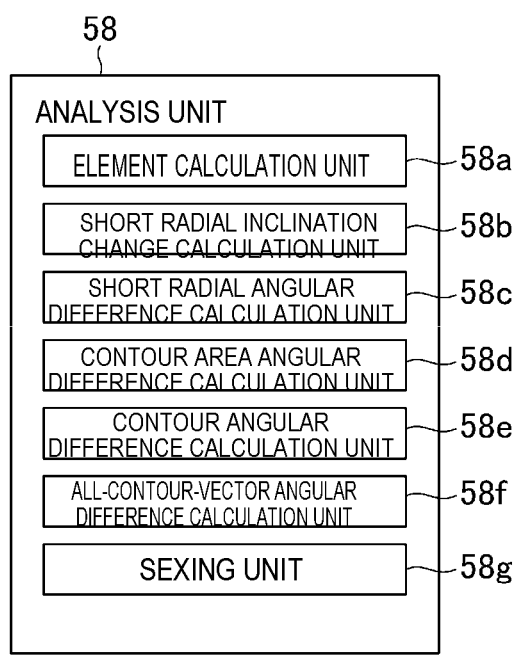

In FIG. 10, the configuration of a control system of the fertilized egg sexing apparatus according to the first embodiment of the present invention is shown and described in detail.

As shown in FIG. 10, the fertilized egg sexing apparatus is provided with three cameras 50, 51 and 52 arranged to be capable of photographing at different photographing angles. Three axes of a placement stand 70 on which the inspection target fertilized egg 10 is placed are adjusted by a horizontal angle adjustment mechanism 64, a rotation angle control adjustment mechanism 65 and a height adjustment mechanism 66. The horizontal angle, rotation angle and height of the placement stand 70 are controlled by an angle control unit 60 according to the attitude and size of the fertilized egg so that the center of the long axis (the long radial) corresponds to an intersection of optical axes of the three cameras 50, 51 and 52.

The fertilized egg sexing apparatus is provided with a control unit 53 that is responsible for overall control. The control unit 53 is connected to a display unit 67, an operation unit 68 and a storage unit 69. By executing a program stored in the storage unit 69, the control unit 53 functions as a 0-degree contour generation unit 54, a 45-degree contour generation unit 55, a 90-degree contour generation unit 56, a three-sided contour combining unit 57, an analysis unit 58 and an angle command unit 59. The angle command unit 59 is connected to the angle control unit 60. The angle control unit 60 is connected to the horizontal angle adjustment mechanism 64 via a wave driver 61, connected to the rotation angle control adjustment mechanism 65 via a rotation driver 62 and connected to the height adjustment mechanism 66 via a lift driver 63. Note that the control unit 53 is realized by a computer or the like.

As for a configuration of a photographing system, the three cameras 50, 51 and 52 arranged to be capable of photographing at different photographing angles are provided. The long and short axes of the fertilized egg are assumed as X and Y axes, and an axis perpendicular to the X and Y axes is assumed as a Z axis; the camera 51 (a center camera) is installed above a two-dimensional plane defined by the X and Y axes and above the Z axis of the fertilized egg, which is a part where the X and Y axes intersect; and the camera 50 (a left camera) and the camera 52 (a right camera) are installed such that optical axes are inclined at the angle of 45 degrees on one side and the other side on the Y axis relative to the Z axis above the two-dimensional plane, and both of the optical axes on the one side and the other side intersect with the Y axis at the center of the fertilized egg existing on the two-dimensional plane. Photographing by the camera 50 (the left camera) is referred to as photographing at the angle of 0 degrees; photographing by the camera 51 (the center camera) is referred to as photographing at the angle of 45 degrees; and photographing by the camera 52 (the right camera) is referred to as photographing at the angle of 90 degrees.

In such a configuration, pieces of image data obtained by image pickup by the three cameras, the camera 50 (with a photographing angle of 0 degrees), the camera 51 (with a photographing angle of 45 degrees) and the camera 52 (with a photographing angle of 90 degrees) are sent to the 0-degree contour generation unit 54, 45-degree contour generation unit 55 and 90-degree contour generation unit 56 of the control unit 53, respectively. Then, at the units 54, 55 and 56, pieces of contour data based on the pieces of image data obtained by photographing at the angle of 0 degrees, the angle of 45 degrees and the angle of 90 degrees (0-degree contour data, 45-degree contour data and 90-degree contour data), respectively, coordinate data and the like are generated. Each of these pieces of contour data is sent to the three-sided contour combining unit 57, and three-sided contour combining of the 0-degree data, the 45-degree data and the 90-degree data is performed. Then, the analysis unit 58 analyzes each piece of contour data and the combined three-sided contour data.

More specifically, the analysis unit 58 of the control unit 53 functions as an element calculation unit 58a, a short radial inclination change calculation unit 58b, a short radial angular difference calculation unit 58c, a contour area angular difference calculation unit 58d, a contour angular difference calculation unit 58e, an all-contour-vector angular difference calculation unit 58f and a sexing unit 58g.

The element calculation unit 58a calculates elements required for calculation at each unit (for example, long radial, short radial, area, short radial inclination, long radial inclination and the like). The short radial inclination change calculation unit 58b calculates the changes in the inclinations of the short radials of an inspection target fertilized egg. The short radial angular difference calculation unit 58c calculates angular differences of the short radial of the fertilized egg. The contour area angular difference calculation unit 58d calculates angular differences of the contour area of the fertilized egg. The contour angular difference calculation unit 58e calculates angular differences of the contour of the fertilized egg. The all-contour-vector angular difference calculation unit 58f calculates angular differences for all contour vectors. Then, the sexing unit 58g performs sexing of the fertilized egg using at least any of calculation results of the units 58a to 58f and outputs a sexing result.

Then, an analysis result by the analysis unit 58 is stored into the storage unit 69. Furthermore, the sexing result of the inspection target fertilized egg is displayed on the display unit 57.

In the process of analysis by the analysis unit 58, the angle command unit 59 sends out a control signal related to driving of the placement stand 70 to the angle control unit 60, and the angle control unit 60 sends out control signals to the wave driver 61, the rotation driver 62 and the lift driver 63. The wave driver 61, the rotation driver 62 and the lift driver 63 drive the horizontal angle adjustment mechanism 64, the rotation angle control adjustment mechanism 65 and the height adjustment mechanism 66 based on the control signals.

Figure 11:
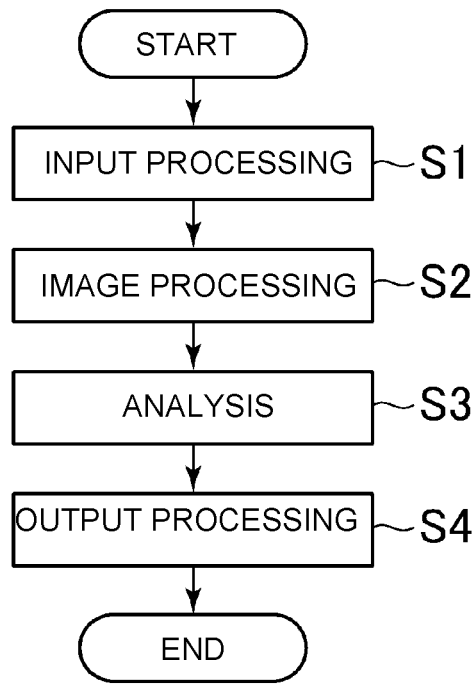
FIG. 11 is a flowchart illustrating a process procedure by the fertilized egg sexing apparatus according to the first embodiment of the present invention.

Hereinafter, a process procedure by the fertilized egg sexing apparatus according to the first embodiment of the present invention will be described with reference to a flowchart of FIG. 11. At least a part of this process procedure corresponds to the fertilized egg sexing method according to the first embodiment of the present invention.

When the process is started, the control unit 53 receives input of image data from each of the cameras 50 to 52 and performs processing (S1). Then, the image data is sent to the 0-degree contour generation unit 54, 45-degree contour generation unit 55 and 90-degree contour generation unit 56 of the control unit 53, and contour data (coordinate data on the XY plane and the like) is generated at each unit. The contour data is sent to the three-sided contour combining unit 57, where three-sided contour combining of 0-degree contour data, 45-degree contour data and 90-degree contour data is performed (S2).

Then, the analysis unit 58 analyzes each piece of contour data and the combined three-sided contour data (S3). Specifically, the element calculation unit 58a calculates elements required for calculation at each unit (for example, the contour vectors, long radials, short radials, areas, short radial inclinations, long radial inclinations and the like defined before). The short radial inclination change calculation unit 58b calculates the changes in the inclinations of the short radials of an inspection target fertilized egg. The short radial angular difference calculation unit 58c calculates short radial angular differences of the fertilized egg. The contour area angular difference calculation unit 58d calculates contour area angular differences of the fertilized egg. The contour angular difference calculation unit 58e calculates contour angular differences of the fertilized egg. The all-contour-vector angular difference calculation unit 58f calculates angular differences for all contour vectors. Then, the sexing unit 58g performs sexing of the fertilized egg using at least any of calculation results of the units 58a to 58f (S3). Thus, a sexing result is displayed on the display unit 67 (S4), and a series of processes related to fertilized egg sexing is completed.

As described above, according to the first embodiment of the present invention, the following technique is realized.

(1-1) A fertilized egg sexing method for making a female/male judgment based on the contour of the egg, wherein the female/male judgment is made using changes in the photographing angular difference of a contour vector average value in a three-dimensional space due to contour distortions obtained by photographing the contour of an inspection target fertilized egg at different angles.

(1-2) A fertilized egg sexing method for making a female/male judgment based on the contour of the egg, wherein the female/male judgment is made using changes in the photographing angular difference of a contour area in a three-dimensional space due to contour distortions obtained by photographing the contour of an inspection target fertilized egg at different angles.

(1-3) The fertilized egg sexing method in (1-1) or (1-2) described above, wherein sexing is performed using the fact that the contour vector average values and the contour areas on the surface of the fertilized egg show a spiral in different directions between female and male eggs, around the long radial connecting the dull end and the sharp end of the fertilized egg.

(1-4) The fertilized egg sexing method in (1-3) described above, wherein, when the long axis connecting the dull end and the sharp end of the fertilized egg is assumed as an X axis, a short axis orthogonal to the long axis is assumed as a Y axis, and an axis orthogonal to the X and Y axes at the intersection between the X and Y axes is assumed as an X axis, sexing of the fertilized egg is performed using the fact that, on an X-Y two-dimensional plane seen from above the Z axis, the contour distortion on the contour of the fertilized egg around the X axis changes along rotation around the X axis, and the contour distortion is in opposite direction between female and male eggs.

(1-5) The fertilized egg sexing method in (1-4) described above, wherein the contour distortion is such that changes in vector data of lines extending from the intersection between the X and Y axes of the fertilized egg to the contour of the fertilized egg at angles θ divided in advance, on the X-Y two-dimensional plane, is formed in a three-dimensional space in the Z axis direction along rotation around the X axis.

(1-6) The fertilized egg sexing method in (1-3) described above, wherein the contour distortion is such that an area change in each of four quadrants of the two-dimensional plane formed by the X and Y axes along rotation around the X axis of the fertilized egg is formed in a three-dimensional space in the Z axis direction along the rotation around the X axis.

(1-7) The fertilized egg sexing method in (1-3) described above, wherein data for indicating the contour distortion is generated from image data generated from an image pickup signal of such a camera that the X axis corresponds to the optical axis above the two dimensional plane defined by the X and Y axes of the fertilized egg and on the Z axis, and image data generated from image pickup signals from a pair of side cameras arranged such that optical axes are inclined at an angle φ set in advance on one side and the other side on the Y axis relative to the Z axis, above the two-dimensional plane relative to the Z axis, and both of the optical axes on the one and other sides intersect with the Y axis at the center of the fertilized egg existing on the two-dimensional plane.

(1-8) A fertilized egg sexing apparatus for executing the methods of (1-1) to (1-7) described above, a program or a computer-readable storage medium storing the program.

Second Embodiment

A second embodiment of the present invention is, for example, characterized in the following.

(b-1) To photograph the external shape (the contour of the shell) of an inspection target fertilized egg with a plurality of cameras to three-dimensionally acquire image data, convert the image data to detailed contour data, calculate short radials of the contour, calculate phase differences of the short radial, and perform sexing of the fertilized egg based on the phase differences.

(b-2) To photograph the external shape (the contour of the shell) of an inspection target fertilized egg with a plurality of cameras to three-dimensionally acquire image data, convert the image data to detailed contour data, calculate short radial inclinations of the contour, calculate logical products of the short radial inclinations and perform sexing of the fertilized egg based on the logical products.

(b-3) To photograph the external shape (the contour of the shell) of an inspection target fertilized egg with a plurality of cameras to three-dimensionally acquire image data, convert the image data to detailed contour data, calculate area distortions and short radial inclinations of the contour, calculate logical products of the area distortions and the short radial inclinations, and perform sexing of the fertilized egg based on the logical products.

The second embodiment of the present invention will be described below in detail. Note that the various kinds of definitions such as a ring distortion, the hardware configurations and the like described in the first embodiment before are also applied to the present embodiment. For example, a viewpoint of sexing by a fertilized egg sexing apparatus according to the second embodiment of the present invention, that is, the fact that differences between the contour of an egg and contour distortion of the egg are different depending on whether the egg is a female egg (♀) or a male egg (♂) is similar to the description made with reference to FIGS. 1(a) to 1(d) before. Therefore, duplicated description will be omitted.

First, a basic structure of a fertilized egg to be an inspection target will be described with reference to FIG. 12.

Figure 12:
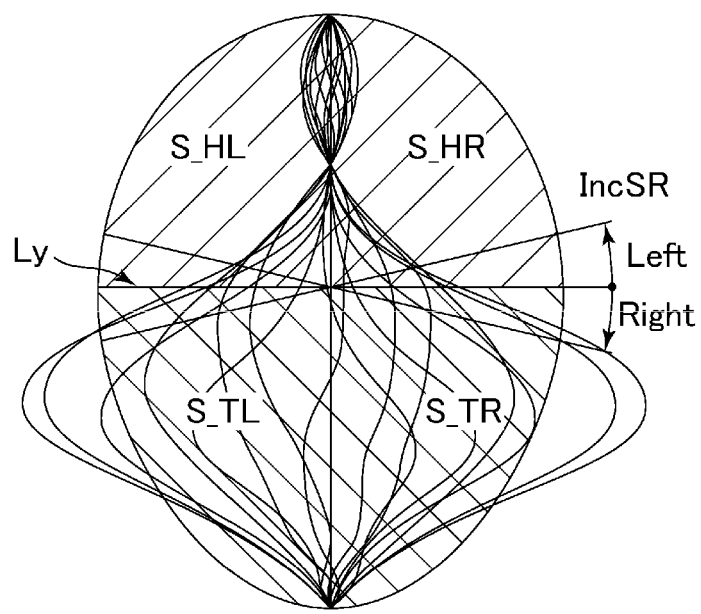
FIG. 12 is a diagram illustrating a basic structure of a fertilized egg to be an inspection target.

When photographing is performed while an egg being rotated to the right by 360 degrees around the long axis of the egg, the inclination of the short radial relative to the long axis of the egg changes as shown in FIG. 12. In FIG. 12, a case where the short radial is inclined to the lower left is expressed as Left, and a case where the short radial is inclined to the lower right is expressed as Right. For example, if, as described before, the long and short axes of a fertilized egg are assumed as X and Y axes, and an axis perpendicular to the X and Y axes is assumed as a Z axis, a center camera is installed above a two-dimensional plane defined by the X and Y axes and above the Z axis of the fertilized egg, which is a part where the X and Y axes intersect; and a left camera and a right camera are installed such that optical axes are inclined at the angle of 45 degrees on one side and the other side on the Y axis relative to the Z axis above the two-dimensional plane, and both of the optical axes on the one side and the other side intersect with the Y axis at the center of the fertilized egg existing on the two-dimensional plane, then, the "inclination of the short radial" refers to a short radial inclination on the two-dimensional plane when seen from an optical axis direction. When the short radial is inclined downward to the right on the two-dimensional plane when seen from the optical axis direction, the inclination is referred to as Right. When the short radial is inclined downward to the left, the inclination is referred to as Left. By the short radial being inclined to the lower left or right, a length Ly of the short radial also changes. As a result, a relationship between area distortions of the head and tail of the egg changes.

The short radial inclination and a head area distortion HLMC are in an in-phase relationship, and the head area distortion HLMC and a tail area distortion TLMC are in an anti-phase relationship. A relationship between the short radial inclination IncSR and the tail area distortion TLMC is reversed at 180 degrees. When short radial phase differences are determined, it is apparent that the phase differences are reversed at intervals of 90 degrees, and the phase differences are opposite between a female egg and a male egg. Therefore, by combining logical products of short radial inclination and area distortion, sexing becomes possible in the four quadrants (at intervals of 90 degrees).

Here, by a right-side area on the head side of the short radial S_HR, a left-side area on the head side of the short radial S_HL, a right-side area on the tail side of the short radial S_TR and a left-side area on the tail side of the short radial S_TL, the head area distortion HLMC and the tail area distortion TLMC are defined as follows:

$$HLMC = S\_HR - S\_HL$$

$$TLMC = S\_TR - S\_TL$$

Furthermore, by a short radial Ly0 by photographing at the angle of 0 degrees and a short radial Ly90 by photographing at the angle of 90 degrees, a phase difference of the short radial is defined as follows:

$$PD\_YRL = Ly0 - Ly90$$

Here, in this embodiment also, the photographing system is provided with a plurality of cameras arranged so that photographing at different photographing angles is possible; the long and short axes of a fertilized egg are assumed as X and Y axes, and an axis perpendicular to the X and Y axes is assumed as a Z axis; an optical axis is inclined at the angle of 45 degrees on each of one side and the other side on the Y axis relative to the Z axis, above a two-dimensional plane defined by the X and Y axes; photographing on the one side is assumed as photographing at the angle of 0 degrees; and photographing on the other side is assumed as photographing at the angle of 90 degrees. In other words, for example, when a description is made using the configuration in FIG. 10 shown before, photographing by the camera 50 (the left camera) is photographing at the angle of 0 degrees, photographing by the camera 51 (the center camera) is photographing at the angle of 45 degrees, and photographing by the camera 52 (the right camera) is photographing at the angle of 90 degrees.

By the short radial inclinations IncSR0 and IncSR90 obtained by photographing at the angle of 0 degrees and photographing at the angle of 90 degrees, the logical product of short radial inclinations is defined as follows:

$$AIP\_SRRL = \text{and}(IncSR0, IncSR90)$$

Next, a definition of a contour vector will be described with reference to FIG. 13.

Figure 13:
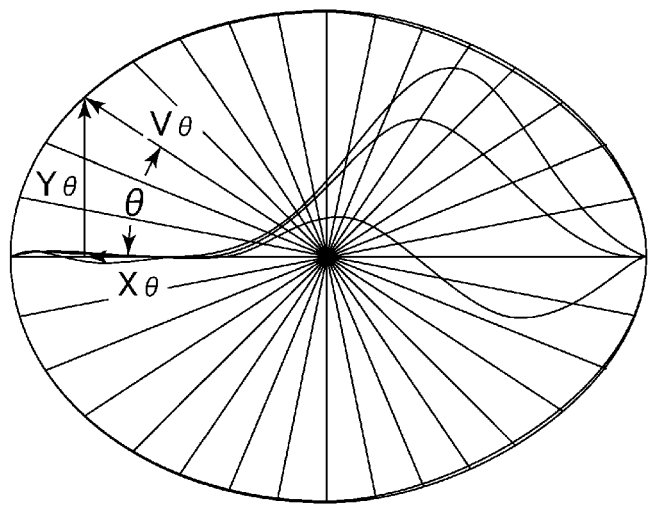
FIG. 13 is a diagram illustrating a definition of the contour vector.

In the present embodiment, distances of radial lines separated at arbitrarily angles from the center of an inspection target egg to intersections with a contour line are defined as contour vectors, and a value obtained by integrating the line segments is defined as TRA as shown in FIG. 13. Specifically, TRA is defined as follows:

$$V_\theta = \sqrt{x_\theta^2 + y_\theta^2} \quad [\text{Equation 6}]$$

$$TRA_R = \sum_{\theta=0°}^{\theta=180°} V_\theta$$

$$TRA_L = \sum_{\theta=360°}^{\theta=180°} V_\theta$$

$$TRA = (TRA_R + TRA_L)/2$$

In other words, a value obtained by determining a difference between contour vectors calculated from pieces of image data obtained by photographing at angles different by 90 degrees is $$PD\_TRARL(PD\_TRARL = TRA0 - TRA90).$$

Next, a definition of a reference contour vector will be described with reference to FIG. 14.

Figure 14:
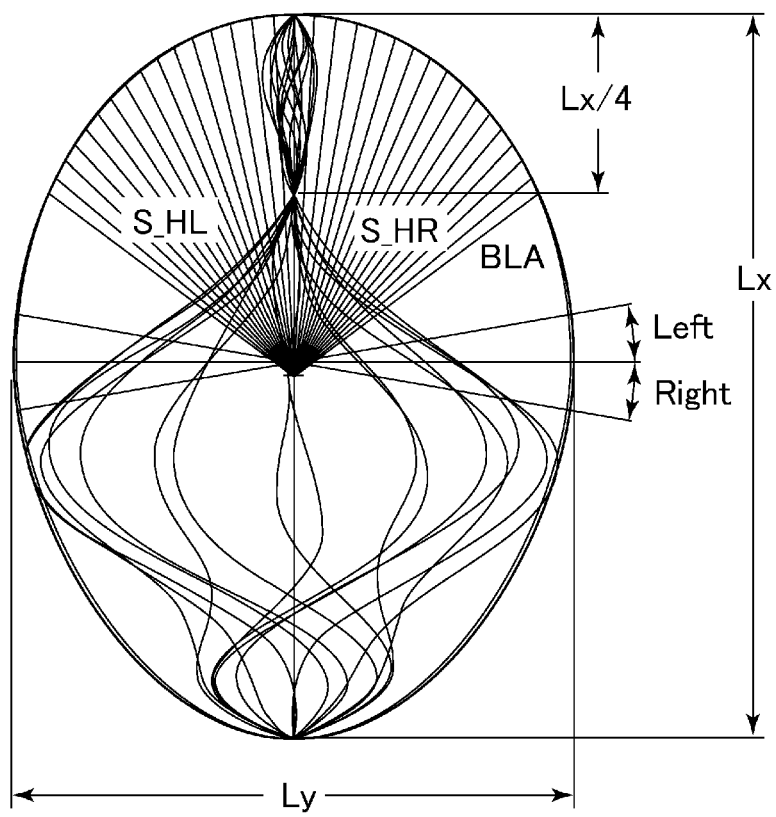
FIG. 14 is a diagram illustrating a definition of a reference contour vector.

In FIG. 14, contour distortions of an egg are superimposedly shown together with the contour of the egg. In FIG. 14, at a position corresponding to Lx/4 from a head top on a long axis Lx, the contour distortions converge to zero. Therefore, in the present embodiment, a contour vector at the point where the contour distortions are zero is defined as a reference vector BLA, and vector distortions from the head top to a reference point (indicated by hatching in FIG. 14) is defined as FLMC.

Here, by reference vectors BLA0, BLA45 and BLA90 defined on pieces of image data obtained by photographing at the angles of 0 degrees, 45 degrees and 90 degrees, respectively, reference vector phase differences are defined as follows:

$$PD\_BLARL = BLA0 - BLA90$$

$$PD\_BLARC = BLA0 - BLA45$$

$$PD\_BLARL = BLA45 - BLA90$$

Next, a spiral structure of an egg will be described with reference to FIG. 15.

Figure 15:
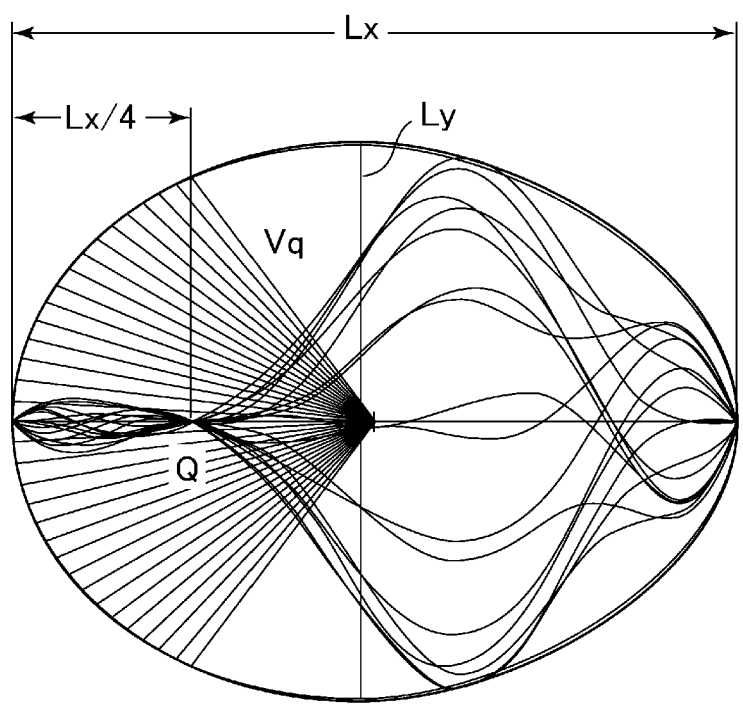
FIG. 15 is a diagram illustrating a spiral structure of an egg.

In FIG. 15, contour distortions of an egg are superimposedly shown together with the contour of the egg. When the egg is observed from the head top, the egg is not in a complete circular shape but is slightly oval. Furthermore, the long axis of the oval gradually and continuously rotates from the head top toward the tail top. This is the spiral structure of the egg.

Meanwhile, in order to accurately detect the head top of the egg, left and right contour vectors Vq at the point corresponding to ¼ of the long axis Lx from the head top are balanced. As a result, the contour distortions converge to zero as shown in FIG. 15. From such a viewpoint, sexing of an egg becomes possible by taking correlation between the vectors Vq and the short radial Ly.

Hereinafter, viewpoints of sexing by the fertilized egg sexing apparatus according to the present embodiment on the assumption of the above definitions will be described in detail based on experimental data.

First, a first viewpoint of sexing will be described with reference to FIGS. 16(a) to 16(d) and FIGS. 17(a) to 17(c).

Figure 16A:
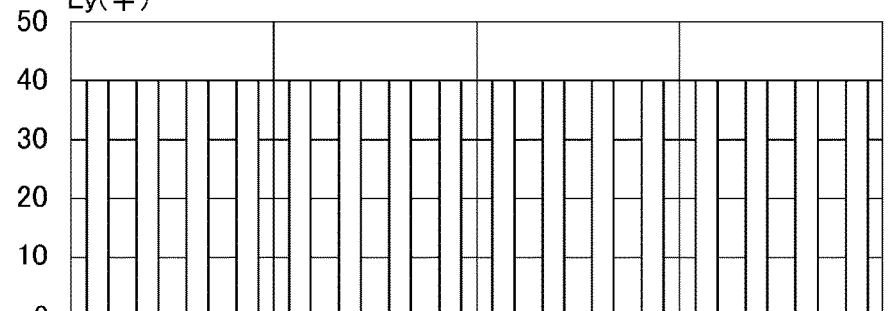
FIGS. 16(a) to 16(d) are diagrams illustrating a first viewpoint of sexing by a fertilized egg sexing apparatus according to a second embodiment of the present invention.
Figure 16B:
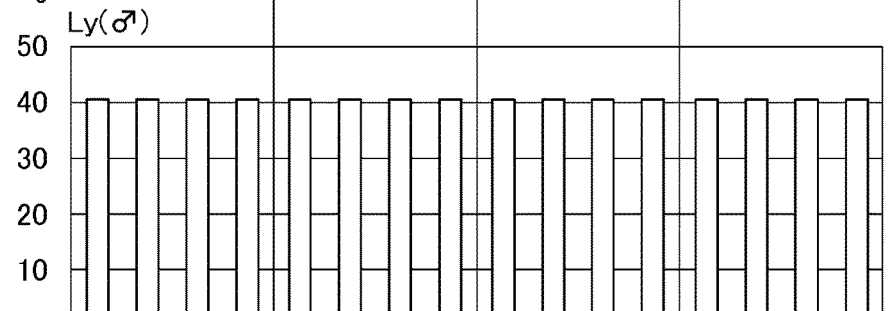
Figure 16C:
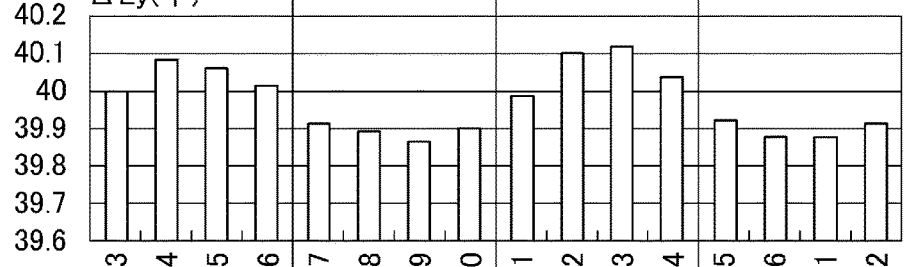
Figure 16D:
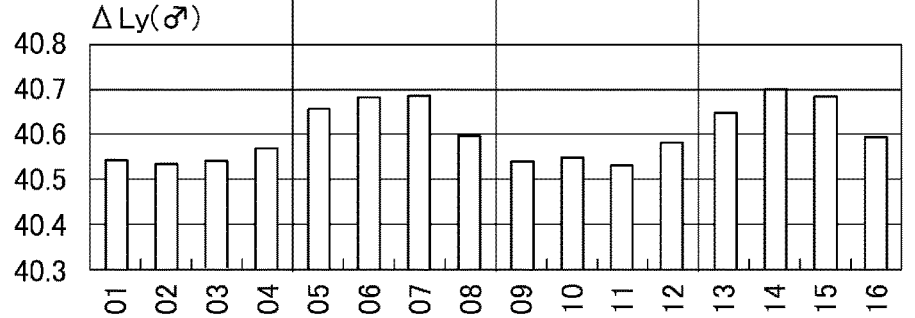

FIG. 16(a) shows the short radial Ly of a female egg; FIG. 16(b) shows the short radial Ly of a male egg; FIG. 16(c) shows differences among values of the short radial of the female egg obtained by a plurality of cameras; and FIG. 16(d) shows differences among values of the short radial of the male egg obtained by a plurality of cameras. As is apparent from these figures, the short radial Ly slightly changes when each egg is photographed, being rotated by 360 degrees. Then, when the changes (differences) are enlarged, the characteristics are different between female and male eggs.

FIG. 17(a) shows short radials Ly0 calculated from image data obtained by photographing the female egg at the angle of 0 degrees; FIG. 17(b) shows short radials Ly90 calculated from image data obtained by photographing the female egg at the angle of 90 degrees; and FIG. 17(c) shows short radial phase differences PD_YRL. As apparent from these figures, when the short radial differences are calculated at intervals of 90 degrees, difference characteristics are reversed in the four quadrants. By performing a similar operation for the male egg, too, characteristics in the four quadrants can also be obtained for the male egg, but phases of the characteristics of the female and male eggs are reversed. Therefore, it becomes possible to perform sexing of a fertilized egg by using the characteristics. The short radial phase difference PD_YRL at 90 degrees corresponds to the rotation direction of the spiral structure of an egg.

Next, a second viewpoint of sexing will be described with reference to FIGS. 18(a) to 18(d) and FIGS. 19(a) to 19(d).

FIG. 18(a) shows short radial inclinations IncSR0 calculated from image data obtained by photographing the female egg at the angle of 0 degrees; FIG. 18(b) shows short radials Ly0 calculated from the image data obtained by photographing the female egg at the angle of 0 degrees; FIG. 18(c) shows short radials Ly90 calculated from image data obtained by photographing the female egg at the angle of 90 degrees; and FIG. 18(d) shows short radial phase differences PD_YRL.

Similarly, FIG. 19(a) shows short radial inclinations IncSR0 calculated from image data obtained by photographing the male egg at the angle of 0 degrees; FIG. 19(b) shows short radials Ly0 calculated from the image data obtained by photographing the male egg at the angle of 0 degrees; FIG. 19(c) shows short radials Ly90 calculated from image data obtained by photographing the male egg at the angle of 90 degrees; and FIG. 19(d) shows short radial phase differences PD_YRL.

In these figures, the short radial Ly0 is a characteristic based on the short radial inclination IncSR0 as a reference. When the phase of the short radial Ly0 is advanced by 90 degrees (Ly90), and the phase difference PD_YRL is calculated, phases of the male and female characteristics are reversed in all of the four quadrants. The same goes for the case of using image data obtained by installing a plurality of cameras at intervals of 90 degrees. Therefore, according to the short radial phase differences PD_YRL, it is possible to perform sexing of a fertilized egg. Note that the short radial phase difference PD_YRL at the angle of 90 degrees corresponds to the rotation direction of the spiral structure of an egg.

Next, a third viewpoint of sexing will be described with reference to FIGS. 20(a) to 20(e).

FIG. 20(a) shows short radial inclinations IncSR0 calculated from image data obtained by photographing a female egg at the angle of 0 degrees; FIG. 20(b) shows short radial inclinations IncSR90 calculated from image data obtained by photographing the female egg at the angle of 90 degrees; FIG. 20(c) shows logical products AIP_SRRL of the short radial inclinations IncSR0 and IncSR90; FIG. 20(d) shows short radial phase differences PD_YRL of the female egg; and FIG. 20(e) shows short radial phase differences PD_YRL of a male egg.

Similarly to the description made with reference to FIG. 12 before, when photographing is performed while an egg being rotated to the right by 360 degrees around the long axis of the egg, the inclination of the short radial of the egg changes as in FIG. 12. By the short radial being inclined to the lower left or right, the length also changes. As a result, area distortions of the head and the tail change. Then, when the phase of the inclination IncSR0 is advanced by 90 degrees (IncSR), and a logical product AIP_SRRL of both is determined, it is apparent that the characteristic is reversed at intervals of 90 degrees. Since this characteristic is the same kind of characteristic as the short radial phase difference PD_YRL, the characteristic of the logical product AIP_SRRL can be used for sexing similarly to the short radial phase difference PD_YRL.

Next, a fourth viewpoint of sexing will be described with reference to FIG. 21.

In FIG. 21, short radials extracted from pieces of image data of sixteen side photographed at intervals of 22.5 degrees while each of one male egg and one female egg being rotated by 360 degrees, and measured values such as inclinations of the short radials are listed. From FIG. 21, as for a logical product AIP_TS0 of the tail area distortion and the short radial inclination, characteristics of the female and male eggs are clearly different, that is, IP (in-phase) and AP (anti-phase), and, therefore, it is apparent that the logical product can be used for sexing of a fertilized egg.

Next, in FIGS. 22(a) to 22(d) and FIGS. 23(a) to 23(f), measurement results according to the present embodiment are shown and described.

Note that FIGS. 22(a) to 22(d) show measurement results based on image data obtained by manual photographing by one camera, and FIGS. 23(a) to 23(f) show measurement results based on image data obtained by automatic photographing by a plurality of cameras.

In these figures, Egg-No indicates a number given to each egg. The first two digits of W30 or the like indicates a week age, and it is meant that, the smaller the number following W is, the younger the week age is.

Week ages, measurement dates and systems (manual/automatic) are as follows:

TABLE 1

| WEEK AGE | MEASUREMENT DATE | SYSTEM |
|---|---|---|
| W 30 | 2008 Jun. 7 | MANUAL |
| W 43 | 2008 Sep. 6 | MANUAL |
| W 46 | 2008 Sep. 27 | MANUAL |
| W 47 | 2009 Oct. 21 | MANUAL |
| W 36 | 2016 Aug. 26 | AUTOMATIC |

Figure 24:
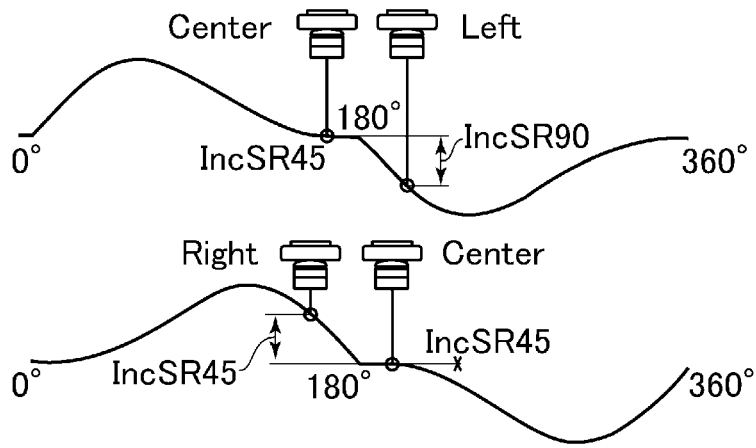
FIG. 24 is a diagram for illustrating unique points.

Here, SEX indicates a sexing result of each egg judged by feather sexing; and SGPT indicates whether a unique point (SGS) or a non-unique point (NoSG). Since it is possible to avoid a sexing error due to a weak signal if a case of detecting a unique point as shown in FIG. 24 and other cases are separated, which is set at the time of sexing is shown. Further, AIP_SRRL indicates a logical product of short radial inclinations (=and (IncSR0, IncSR90)) of the egg, which is an inspection aspect. In the case of in-phase, IP is shown. In the case of anti-phase, AP is shown.

Further, TLMC45 indicates a tail area distortion by photographing at the angle of 45 degrees; IncSR0 indicates a short radial inclination by photographing at the angle of 0 degrees; and IncSR90 indicates a short radial inclination by photographing at the angle of 90 degrees. When the short radial is inclined to the lower left, Left is shown. When the short radial is inclined to the lower right, Right is shown. Further, AIP_XRC indicates a logical product of a distortion direction of a contour vector by photographing at the photographing angle of 0 degrees and a distortion direction of a contour vector by photographing at the photographing angle of 45 degrees.

Further, PD_BLARL indicates a 90-degree phase difference of the reference vector; PD_TRTCL indicates a logical product of an integrated value of contour vectors on the tail side of the short radial by photographing at the photographing angle of 45 degrees and an integrated value of contour vectors on the tail side of the short radial by photographing at the photographing angle of 90 degrees; and PD_F45FB indicates a phase characteristic when the contour vector distortion on the head side of the balance point described before is further separated at intervals of about 27 degrees. It is indicated by Lead that Forward is stronger than Back, and it is indicated by Lag that Forward is weaker than Back. Further, PD_YRL indicates a short radial phase difference (=Ly0−Ly90); and Lag and Lead mean phase lag and phase lead, respectively.

From FIGS. 22(a) and 22(b), it is seen that appropriate sexing is performed based on PD_YRL no matter whether (TLMC45, AIP_XRC) is (Left, IP) or (Left, AP). Further, from FIGS. 22(c) and 22(d), it is seen that appropriate sexing is performed based on PD_YRL no matter whether (TLMC45, PD_BLARL) is (Right, Lead) or (Right, Lag). A sexing result of the egg of W3617 is considered to be an error due to deficiency of the photographing mechanism.

From FIGS. 23(a) and 23(b), it is seen that appropriate sexing is performed based on PD_YRL no matter whether (PD_F45FB, PD_TRTCL) is (Lead, Lead), (Lead, Lag), (Lag, Lag), or (Lag, Lead). Further, in this group, since regularity is seen between the combination of PD_F45FB and PD_TRTCL, and PD_YRL, it is also possible to perform sexing of an egg based on the combination of PD_F45FB and PD_TRTCL.

From FIGS. 23(c) and 23(f), it is seen that appropriate sexing is performed based on PD_YRL no matter whether (PD_F45FB, PD_TRTCL) is (Lead, Lead), (Lead, Lag), (Lag, Lead), or (Lag, Lag). This means that appropriate sexing is possible in any of the four quadrants obtained by separating 360 degrees at intervals of 90 degrees. Note that a sexing result of the egg of W4734 is considered to be an error due to deficiency of the photographing mechanism.

Further, IP is shown for AIP_SRRL in FIGS. 22(a) to 22(d); AP is shown for AIP_SRRL in FIGS. 23(a) to 23(f); and it is seen that appropriate sexing is performed based on PD_YRL in any of the cases.

In this example, for two eggs among the forty-one sample eggs, information about the judgment element PD_YRL is opposite. The information that the information is opposite is a result of judgment based on being contrary to the theorem that four quadrants are reversible. In structural information to reach the judgment, complicated conditions are the same. Moreover, since it is proved that photographing mistakes were made for the two eggs, a judgment mistake does not occur if the photographing mechanism is ideal. This fact occurs due to the fact that the female/male structure of an egg is not influenced by the size and the magnitude of distortion, and it is difficult to think that the sex of the eggs have been changed. Therefore, the present application sufficiently discloses a specific approach for taking the place of the sexing rate of the current anal sexing and feather sexing, and it is possible to obtain a sexing rate equal to the sexing rate of the current anal sexing and feather sexing, that is, 95% to 98%.

A configuration and operation of the fertilized egg sexing apparatus according to the second embodiment of the present invention, which adopts the sexing viewpoints as described before, are almost similar to those of the first embodiment described with reference to FIG. 10 before. However, details of the analysis unit is different from those of the first embodiment. The control unit of the fertilized egg sexing apparatus is realized by a computer or the like.

Figure 25:
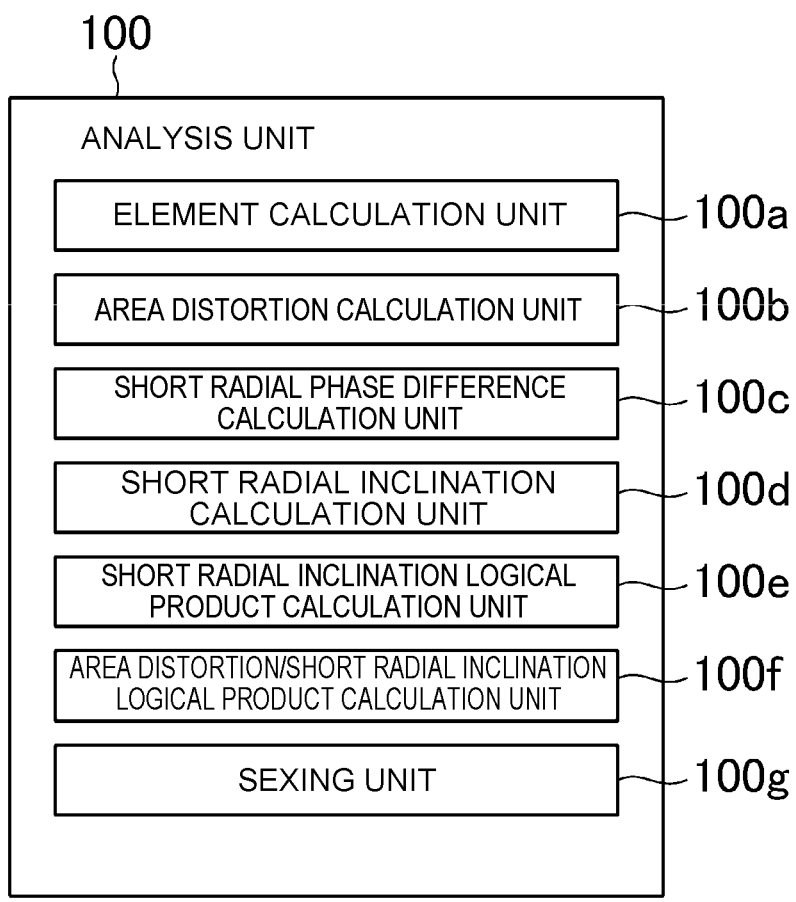
FIG. 25 is a diagram showing a configuration of an analysis unit of the fertilized egg sexing apparatus according to the second embodiment of the present invention.

Therefore, in FIG. 25, a detailed configuration of the analysis unit are shown and described.

An analysis unit 100 of the fertilized egg sexing apparatus according to the second embodiment functions as an element calculation unit 100a, an area distortion calculation unit 100b, a short radial phase difference calculation unit 100c, a short radial inclination calculation unit 100d, a short radial inclination logical product calculation unit 100e, an area distortion/short radial inclination logical product calculation unit 100f and a sexing unit 100g by executing a program in the storage unit 69.

In this embodiment also, the photographing system is provided with a plurality of cameras arranged so that photographing at different photographing angles is possible; the long and short axes of a fertilized egg are assumed as X and Y axes, and an axis perpendicular to the X and Y axes is assumed as a Z axis; an optical axis is inclined at the angle of 45 degrees on each of one side and the other side on the Y axis relative to the Z axis, above a two-dimensional plane defined by the X and Y axes; photographing on the one side is assumed as photographing at the angle of 0 degrees; and photographing on the other side is assumed as photographing at the angle of 90 degrees. For example, when a description is made using the configuration of FIG. 10 shown before, photographing by the camera 50 (the left camera) is photographing at the angle of 0 degrees, photographing by the camera 51 (the center camera) is photographing at the angle of 45 degrees, and photographing by the camera 52 (the right camera) is photographing at the angle of 90 degrees.

In more detail, the element calculation unit 100a calculates elements required for calculation at each unit (for example, contour vector, short radial, long radial, area and the like). The area distortion calculation unit 100b calculates the head area distortion HLMC and the tail area distortion TLMC by the right-side area on the head side of the short radial S_HR, the left-side area on the head side of the short radial S_HL, the right-side area on the tail side of the short radial S_TR and the left-side area on the tail side of the short radial S_TL. The short radial phase difference calculation unit 100c calculates short radial phase differences PD_YRL, PD_YRC and PD_YCL by the short radial Ly0 by photographing at the photographing angle of 0 degrees, the short radial Ly45 by photographing at the photographing angle of 45 degrees, and the short radial Ly90 by photographing at the photographing angle of 90 degrees. The short radial inclination calculation unit 100d calculates short radial inclinations IncSR0, IncSR45 and IncSR90 from image data obtained by photographing at the angles of 0 degrees, 45 degrees and 90 degrees. The short radial inclination logical product calculation unit 100e calculates logical products AIP_SRRL, AIP_SRRC and AIP_SRCL by short radial inclinations. The area distortion/short radial inclination logical product calculation unit 100f calculates logical products of tail area distortions and short radial inclinations by tail area distortions TLMC0, TLMC45 and TLMC90 and the short radial inclinations IncSR0, IncSR45 and IncSR90. Then, the sexing unit 100g performs sexing of a fertilized egg and outputs a result, based on at least any of the calculation results by the units.

Though a process procedure by the fertilized egg sexing apparatus according to the second embodiment of the present invention is almost similar to that described in the first embodiment before, the process of the analysis (S3) is different. In the analysis process, sexing is performed by the above analysis by the units 100a to 100g described before.

According to the second embodiment of the present invention, the following technique is realized.

(2-1) A fertilized egg sexing method for making a female/male judgment according to a contour of a fertilized egg by a computer, the fertilized egg sexing method including: extracting the contour based on image data obtained by photographing the fertilized egg at different angles, calculating a short radial from the contour, calculating phase differences among short radials corresponding to photographing at the angles, and making a female/male judgment using the phase differences among the short radials.

(2-2) The fertilized egg sexing method, wherein, in the female/male judgment of (2-1) described above, the contour is extracted based on the image data, short radial inclinations are calculated from the contour, and a relationship among the short radial inclinations corresponding to photographing at different angles is further used.

(2-3) The fertilized egg sexing method, wherein, in the female/male judgment of (2-1) and (2-2) described above, the contour is extracted based on the image data, area distortions and short radial inclinations are calculated from the contour, and a relationship between the area distortions and the short radial inclinations is further used.

(2-4) A fertilized egg sexing apparatus for executing the methods of (2-1) to (2-3) described above, a program or a computer-readable storage medium storing the program.

As described above in detail, when photographing is performed while an egg being rotated to the right around the long axis of the egg by 360 degrees, inclination in the short radial of the egg changes as shown in FIG. 12 before. In the present invention, the case where the short radial is inclined to the lower left is defined as Left, and the case where the short radial is inclined to the lower right is defined as Right as described before. By the short radial being inclined to the lower left or right, the length also changes. As a result, area distortions of the head and the tail change. Then, when the phase with an inclination of 0 degrees is advanced by 90 degrees, and a logical product of both is determined, it is apparent that the characteristic is reversed at intervals of 90 degrees. For example, FIG. 20(c) shows the logical products AIP_SRRL of the short radial inclinations IncSR0 and IncSR90. Since this characteristic is the same kind as the characteristic of the short radial phase difference, the characteristic of the logical products can be used for sexing similarly to the short radial phase differences. From this viewpoint, it becomes possible to make a female/male judgment using the short radial phase differences and the logical products.

Furthermore, a velocity curve of an egg can be determined by short radial inclinations and it corresponds to the principle of forced oscillation of a pendulum. The value abruptly changes, that is, nonlinearly changes depending on the photographing angle. However, automatic sexing is impossible unless the pattern of the change is identified. Therefore, in the present invention, "short radial inclination" is set as a primary region criterion. A distortion which changes due to the size of an egg and the phase of which does not change is not a parameter that takes the place of the short radial inclination. In the invention of the present application, sexing of an egg is realized by "logical products of short radial inclinations".

Further, the rotation directions of female and male eggs look opposite every 90° (four quadrants). Therefore, a technique for automatically detecting the four quadrants is required for sexing of an egg. Thus, in the present invention, the detection is performed by rotation velocity based on an inclination direction of an egg. In other words, as a specific approach, the four quadrants are determined by logical products of short radial inclinations of an egg. The nonlinear characteristic of an egg is utilized for the logical products, and it is known that especially a parameter having an anti-phase characteristic is also effective for the detection of the four quadrants.

Furthermore, it became clear that, when the inclination IncSR of an egg is used as a reference, the phase of the head area distortion HLMC corresponds to the inclination, and the phase of the tail area distortion TLMC leads by 90 degrees relative to the short radial inclination IncSR in the case of a female egg and lags by 90 degrees in the case of a male egg. Therefore, it became clear that sexing can be also performed based on the tail area distortion. Therefore, by adding area distortions, more accurate sexing is realized.

Further, in the invention of the present application, it is clarified that sexing by three-sided simultaneous photographing is realized for the first time in the world. In general, it is known that the egg size changes by almost 20% during a period from the time a parent hen begins to lay eggs to the time the hen becomes a spent hen. The center of an egg placed on a placement stand also changes due to the change. Accompanying the change, the position of the long axis of the egg changes on the horizontal plane and on the vertical line, which influences photographing. In the invention of the present application, however, the influence is prevented by adjusting the placement stand by the three-axis control unit.

Therefore, according to the fertilized egg sexing apparatus, fertilized egg sexing method and program according to the first and second embodiments of the present invention, it is possible to discriminate female eggs among fertilized eggs in a non-destructive and non-contact manner with a high sexing rate. Therefore, it is possible to transfer eggs other than female eggs, such as female eggs and indiscriminable eggs that are rarely mixed, for vaccine manufacturing or as food material. Since it becomes unnecessary to dispose of hatched male chicks thereby, the ethical problem can be solved. Furthermore, by targeting only female eggs for hatching, half of hatching facilities can be used for increased production of female chicks. Further, by transferring eggs other than female eggs as food material, it is possible to respond to the situation of the global protein deficiency.

The first and second embodiments of the present invention have been described above. The present invention, however, is not limited thereto, and it is, of course, possible to make various improvements and changes within a range not departing from the spirit of the invention.

For example, if the inclination of the long axis of an egg obtained in the process of measurement is equal to or above a predetermined value, a measurement error may be anticipated, and a warning that prompts adjustment or discontinuance of photographing may be issued.

REFERENCE SIGNS LIST

50, 51, 52 Camera
53 Control unit
54 0-degree contour generation unit
55 45-degree contour generation unit
56 90-degree contour generation unit
57 Three-sided contour combining unit
58 Analysis unit
59 Angle command unit
60 Angle control unit
61 Wave driver
62 Rotation driver
63 Lift driver
64 Horizontal angle adjustment mechanism
65 Rotation angle control adjustment mechanism
66 Height adjustment mechanism
67 Display unit
68 Operation unit
69 Storage unit
70 Placement stand

The invention claimed is:

1. A fertilized egg sexing method for making a female/male judgment according to a contour of a fertilized egg by a computer, based on image data obtained by photographing by a plurality of cameras, wherein first and second cameras are installed such that, when long and short axes of the fertilized egg are assumed as X and Y axes, and an axis perpendicular to the X and Y axes is assumed as a Z axis, optical axes are inclined at an angle of 45 degrees on one side and another side on the Y axis relative to the Z axis above a two-dimensional plane defined by the X and Y axes, and both of the optical axes on the one side and the other side intersect with the Y axis at a center of the fertilized egg existing on the two-dimensional plane; and the fertilized egg sexing method comprises: extracting the contour based on image data obtained by photographing the fertilized egg at different angles; calculating a short radial from the contour; calculating a short radial phase difference, which is a difference between the short radial by photographing by the first camera at an angle of 0 degrees and the short radial by photographing by the second camera at an angle of 90 degrees; calculating a logical product of inclinations of the short radials obtained by the photographing by the first camera at the angle of 0 degrees and the photographing by the second camera at the angle of 90 degrees; and making the female/male judgment using the short radial phase difference and the logical product.

2. The fertilized egg sexing method according to claim 1, wherein, in the female/male judgment, a head area distortion, which is a difference between a right-side area on a head side of the short radial and a left-side area on the head side of the short radial, and a tail area distortion, which is a difference between a right-side area on a tail side of the short radial and a left-side area on the tail side of the short radial, are calculated from the contour, with the short radial as a border, and relationships between the head area distortion and the tail area, and the short radial inclinations are further used.

3. A fertilized egg sexing apparatus for making a female/male judgment according to a contour of a fertilized egg, the fertilized egg sexing apparatus comprising:
  first and second cameras installed such that, when long and short axes of the fertilized egg are assumed as X and Y axes, and an axis perpendicular to the X and Y axes is assumed as a Z axis, optical axes are inclined at an angle of 45 degrees on one side and another side on the Y axis relative to the Z axis above a two-dimensional plane defined by the X and Y axes, and both of the optical axes on the one side and the other side intersect with the Y axis at a center of the fertilized egg existing on the two-dimensional plane; and
  a control unit extracting the contour based on image data obtained by photographing the fertilized egg at different angles, calculating a short radial from the contour, calculating a short radial phase difference, which is a difference between the short radial by photographing by the first camera at an angle of 0 degrees and the short radial by photographing by the second camera at an angle of 90 degrees, calculating a logical product of inclinations of the short radials obtained by the photographing by the first camera at the angle of 0 degrees and the photographing by the second camera at the angle of 90 degrees, and making the female/male judgment using the short radial phase difference and the logical product.

4. The fertilized egg sexing apparatus according to claim 3, wherein, in the female/male judgment, the control unit calculates a head area distortion, which is a difference between a right-side area on a head side of the short radial and a left-side area on the head side of the short radial, and a tail area distortion, which is a difference between a right-side area on a tail side of the short radial and a left-side area on the tail side of the short radial, from the contour, with the short radial as a border, and further uses relationships between the head area distortion and the tail area, and the short radial inclinations.

5. The fertilized egg sexing apparatus according to claim 3, comprising:
  a third camera arranged above the two-dimensional plane defined by the X and Y axes and above the Z axis of the fertilized egg at an intersection between the X and Y axes;
  a placement stand for which horizontal angle control, rotation angle control and height control can be performed; and
  a three-axis control unit performing the horizontal angle control, the rotation angle control and the height control; wherein
  the fertilized egg is placed on the placement stand; and
  the three-axis control unit performs servo-control so that the long axis of the fertilized egg seen by the third camera becomes parallel to the X axis, performs the height control so that the short radial of the fertilized egg becomes a fixed value set in advance, drive-controls the placement stand so as to adjust a point at which optical axes of the first and second cameras intersect to the long axis of the fertilized egg; and performs three-sided image photographing by the first to third cameras.

6. A non-transitory computer readable medium storing a computer executable program for making a female/male judgment of a fertilized egg based on image data obtained by photographing by first and second cameras arranged such that, when long and short axes of the fertilized egg are assumed as X and Y axes, and an axis perpendicular to the X and Y axes is assumed as a Z axis, optical axes are inclined at an angle of 45 degrees on one side and another side on the Y axis relative to the Z axis above a two-dimensional plane defined by the X and Y axes, and both of the optical axes on the one side and the other side intersect with the Y axis at a center of the fertilized egg existing on the two-dimensional plane, wherein,
  the program causes a computer to function as a control unit extracting the contour based on image data obtained by photographing the fertilized egg at different angles, calculating a short radial from the contour, calculating a short radial phase difference, which is a difference between the short radial by photographing by the first camera at an angle of 0 degrees and the short radial by photographing by the second camera at an angle of 90 degrees, calculating a logical product of inclinations of the short radials obtained by the photographing by the first camera at the angle of 0 degrees and the photographing by the second camera at the angle of 90 degrees, and making the female/male judgment using the short radial phase difference and the logical product.

7. The non-transitory computer readable medium according to claim 6, wherein, in the female/male judgment, the control unit calculates a head area distortion, which is a difference between a right-side area on a head side of the short radial and a left-side area on the head side of the short radial, and a tail area distortion, which is a difference between a right-side area on a tail side of the short radial and a left-side area on the tail side of the short radial, from the contour, with the short radial as a border, and further uses relationships between the head area distortion and the tail area, and the short radial inclinations.

\* \* \* \* \*